United States Patent
Leong et al.

(10) Patent No.: US 10,910,086 B2
(45) Date of Patent: Feb. 2, 2021

(54) METHODS AND SYSTEMS FOR DETECTING MINOR VARIANTS IN A SAMPLE OF GENETIC MATERIAL

(71) Applicant: Life Technologies Corporation, Carlsbad, CA (US)

(72) Inventors: Harrison Leong, San Francisco, CA (US); Edgar Schreiber, Redwood City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 745 days.

(21) Appl. No.: 15/504,299

(22) PCT Filed: Aug. 14, 2015

(86) PCT No.: PCT/US2015/045371
§ 371 (c)(1),
(2) Date: Feb. 15, 2017

(87) PCT Pub. No.: WO2016/025892
PCT Pub. Date: Feb. 18, 2016

(65) Prior Publication Data
US 2017/0235874 A1    Aug. 17, 2017

Related U.S. Application Data

(60) Provisional application No. 62/120,766, filed on Feb. 25, 2015, provisional application No. 62/092,135, filed on Dec. 15, 2014, provisional application No. 62/038,161, filed on Aug. 15, 2014.

(51) Int. Cl.
| | | |
|---|---|---|
| *G01N 33/48* | (2006.01) | |
| *G16B 20/00* | (2019.01) | |
| *G16B 40/00* | (2019.01) | |
| *G06G 7/58* | (2006.01) | |

(52) U.S. Cl.
CPC ............. *G16B 20/00* (2019.02); *G16B 40/00* (2019.02)

(58) Field of Classification Search
None
See application file for complete search history.

(56) References Cited

U.S. PATENT DOCUMENTS

| 5,981,186 A | 11/1999 | Gabe et al. |
| 7,912,652 B2 | 3/2011 | Sorenson |
| 2012/0116688 A1 | 5/2012 | Mishra et al. |

FOREIGN PATENT DOCUMENTS

WO    2003036434 A2    5/2003

OTHER PUBLICATIONS

Peterson, Thomas A., et al., Towards Precision Medicine: Advances in Computational Approaches for the Analysis of Human Variants, J. Mol. Biol., 2013, pp. 4047-4063, vol. 425, Elsevier Ltd.
International Search Report and Written Opinion issued in International Application No. PCT/US2015/045371 dated Dec. 10, 2015, 13 pages.
Office Action issued in European Application No. 15 762 808.2 dated May 12, 2020, 6 pages.
Carr et al., "Inferring relative proportions of DNA variants from sequencing electropherograms," Bioinformatics, vol. 25, No. 24, 2009, 7 pages.
Office Action issued in Chinese Application No. 20158005277.2 dated Jul. 30, 2020, 28 pages.

*Primary Examiner* — Eric S Dejong
(74) *Attorney, Agent, or Firm* — Mauriel Kapouytian Woods LLP; Liang Huang; Michael Mauriel

(57) ABSTRACT

A computer-implemented method for determining minor variants. The method includes receiving electropherogram sequence data from a test sample, identifying any non-primary peaks in the electropherogram, and characterizing identified non-primary peaks using at least one signal feature. The method may further include analyzing the at least one signal feature across identified non-primary peaks to identify variant candidates, evaluating at least one peak characteristic of each of the identified variant candidates, and classifying variant candidates as bona fide variants based on the evaluation of peak characteristics.

27 Claims, 16 Drawing Sheets

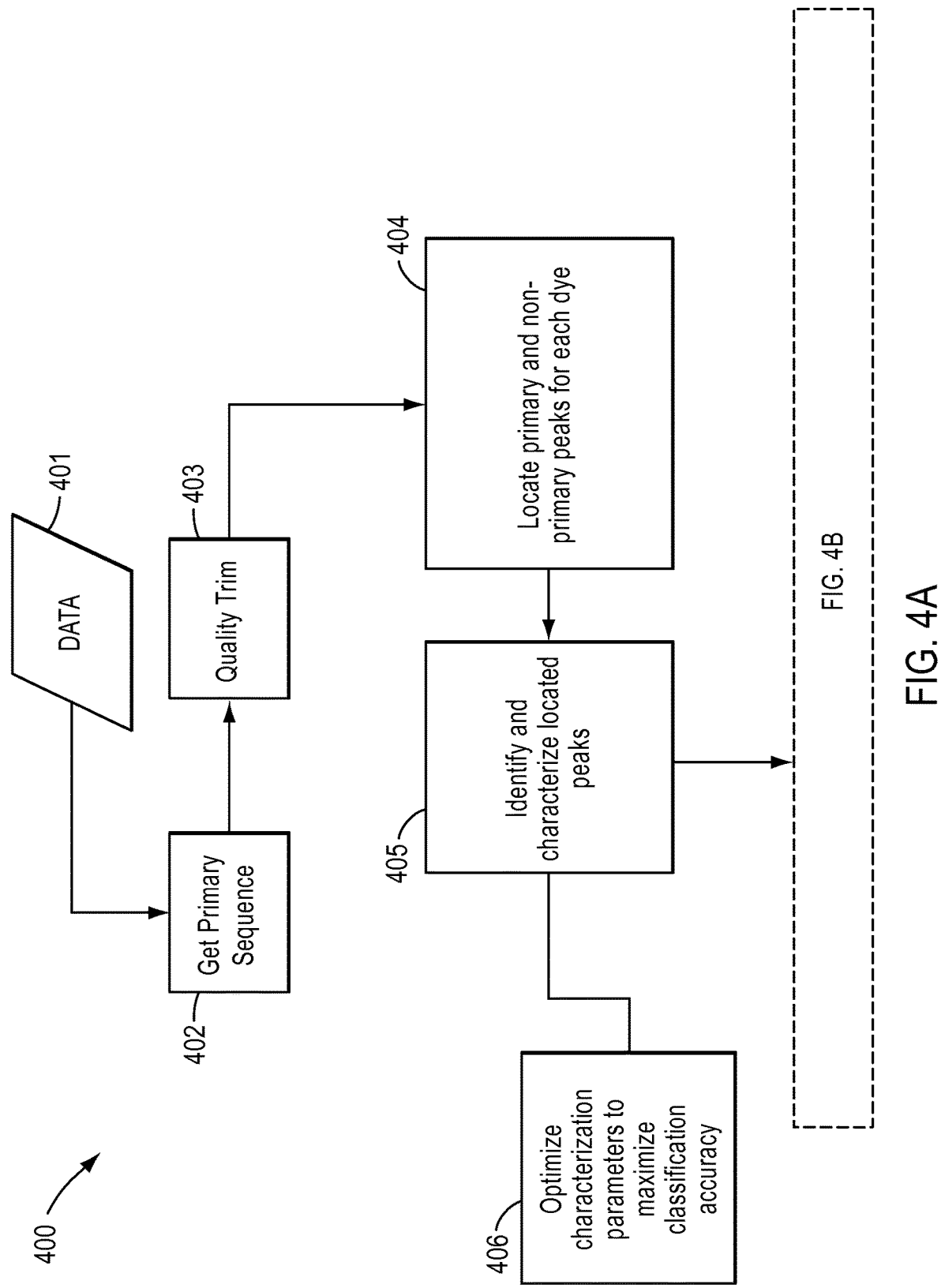

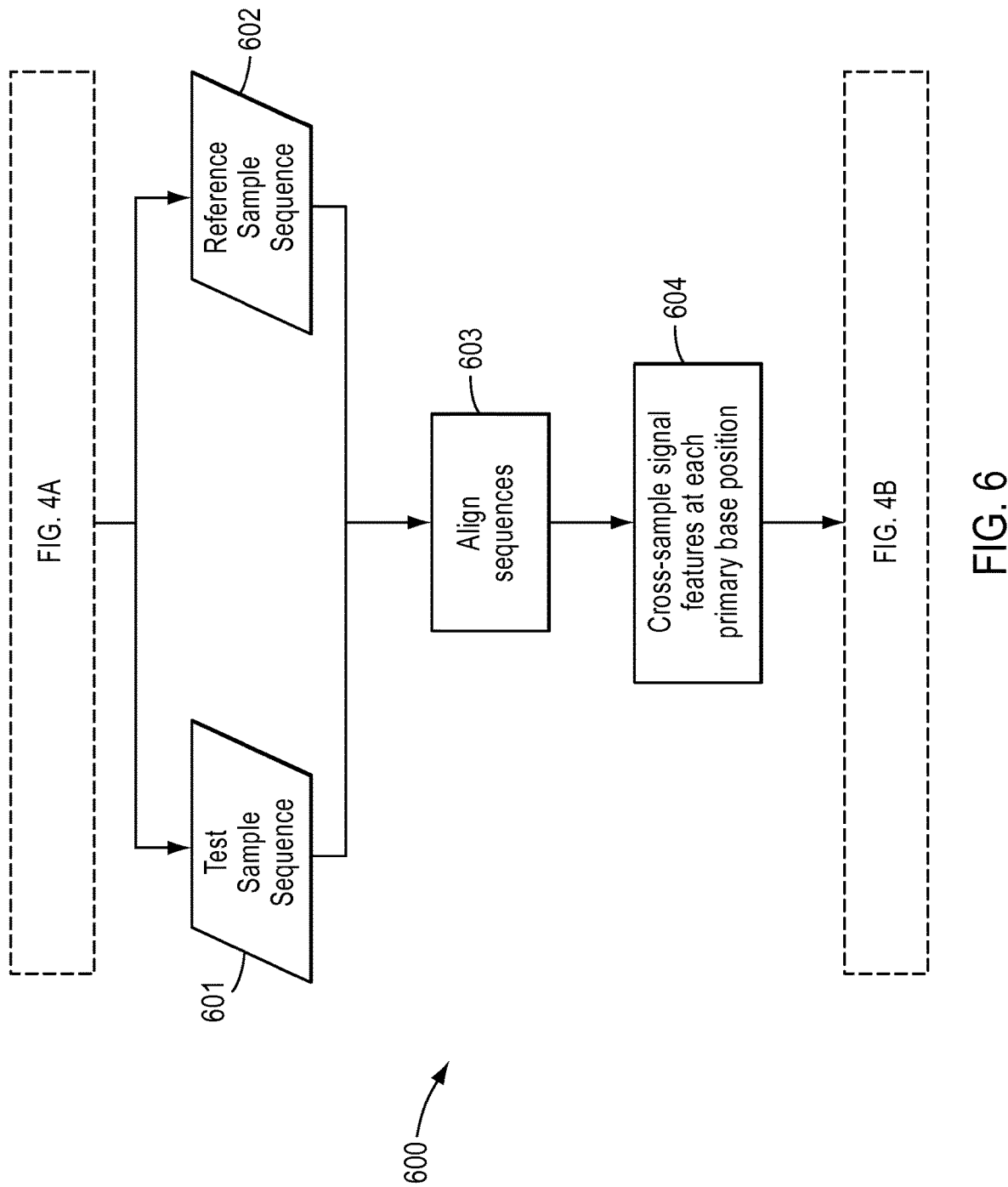

METHODS AND SYSTEMS FOR DETECTING MINOR VARIANTS IN A SAMPLE OF GENETIC MATERIAL

CROSS REFERENCE TO RELATED APPLICATIONS

This application is a 371 national phase of International Application No. PCT/US2015/045371 filed Aug. 14, 2015, which claims priority to U.S. Application No. 62/120,766 filed Feb. 25, 2015, U.S. Application No. 62/092,135 filed Dec. 15, 2014, and U.S. Application No. 62/038,161 filed Aug. 15, 2014. The entire contents of these applications are hereby incorporated herein by reference.

BACKGROUND

Biological analysis devices, including DNA sequencing systems, such as slab-gel and capillary electrophoresis sequencers, often employ a method wherein DNA fragments are separated via migration in a separation medium. Usually labels, e.g., fluorescent dyes, associated with each of the separated fragments are read as the fragments pass through a detection zone. The result is a series of traces, sometimes referred to as an electropherogram, where each trace relates the abundance of the labels over time. Interpretation of the peaks in each trace leads to a determination as to the genetic sequence of the sample. Such interpretation, sometimes referred to as base calling, can be carried out manually or in an automated fashion (e.g., using a programmed computer). The method of interpreting the signal is central to the base calling process and can greatly affect the quality of the results.

A sample of genetic material (DNA or RNA) might contain more than one variation of the genetic material. An example is a sample from a population of viruses where most of the viruses have the same genetic profile but some have slight variations. Another example is a blood sample where most of the genetic material is normal but a few are from cancerous tissue. In these situations most of the genetic material is the same and the bases of the DNA or RNA corresponding to the most common genetic material are called the primary bases. The less common genetic material may have base sequences that are mostly the same as the common material, but differ at a few base positions. These differences may be referred to as minor variants. The methods discussed herein are concerned with accurately detecting and identifying the minor variants in a sample of genetic material.

SUMMARY

The present disclosure relates, in some embodiments, to a computer-implemented method for determining minor variants. The method includes receiving electropherogram sequence data from a test sample, identifying any non-primary peaks in the electropherogram, and characterizing identified non-primary peaks using at least one signal feature. The method may further include analyzing the at least one signal feature across identified non-primary peaks to identify variant candidates, evaluating at least one peak characteristic of each of the identified variant candidates, and classifying variant candidates as bona fide variants based on the evaluation of peak characteristics.

In an embodiment, a non-transitory computer-readable storage medium encoded with instructions, executable by a processor, can be provided. The instructions can comprise instructions for receiving electropherogram sequence data from a test sample, identifying any non-primary peaks in the electropherogram, and characterizing identified non-primary peaks using at least one signal feature. The non-transitory computer-readable storage medium may further include instructions for analyzing the at least one signal feature across identified non-primary peaks to identify variant candidates, evaluating at least one peak characteristic of each of the identified variant candidates, and classifying variant candidates as bona fide variants based on the evaluation of peak characteristics.

In yet another embodiment, a system for determining minor variants is provided. The system can comprise a processor and a memory encoded with instructions, executable by the processor. The instructions can comprise instructions for receiving electropherogram sequence data from a test sample, identifying any non-primary peaks in the electropherogram, and characterizing identified non-primary peaks using at least one signal feature. The instructions may further include instructions for analyzing the at least one signal feature across identified non-primary peaks to identify variant candidates, evaluating at least one peak characteristic of each of the identified variant candidates, and classifying variant candidates as bona fide variants based on the evaluation of peak characteristics.

DESCRIPTION OF THE FIGURES

FIGS. 4A-4B illustrate a workflow for determining minor variants according to embodiments of the present teachings.

FIG. 6 illustrates another workflow for determining minor variants according to embodiments of the present teachings.

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the embodiments.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 1:
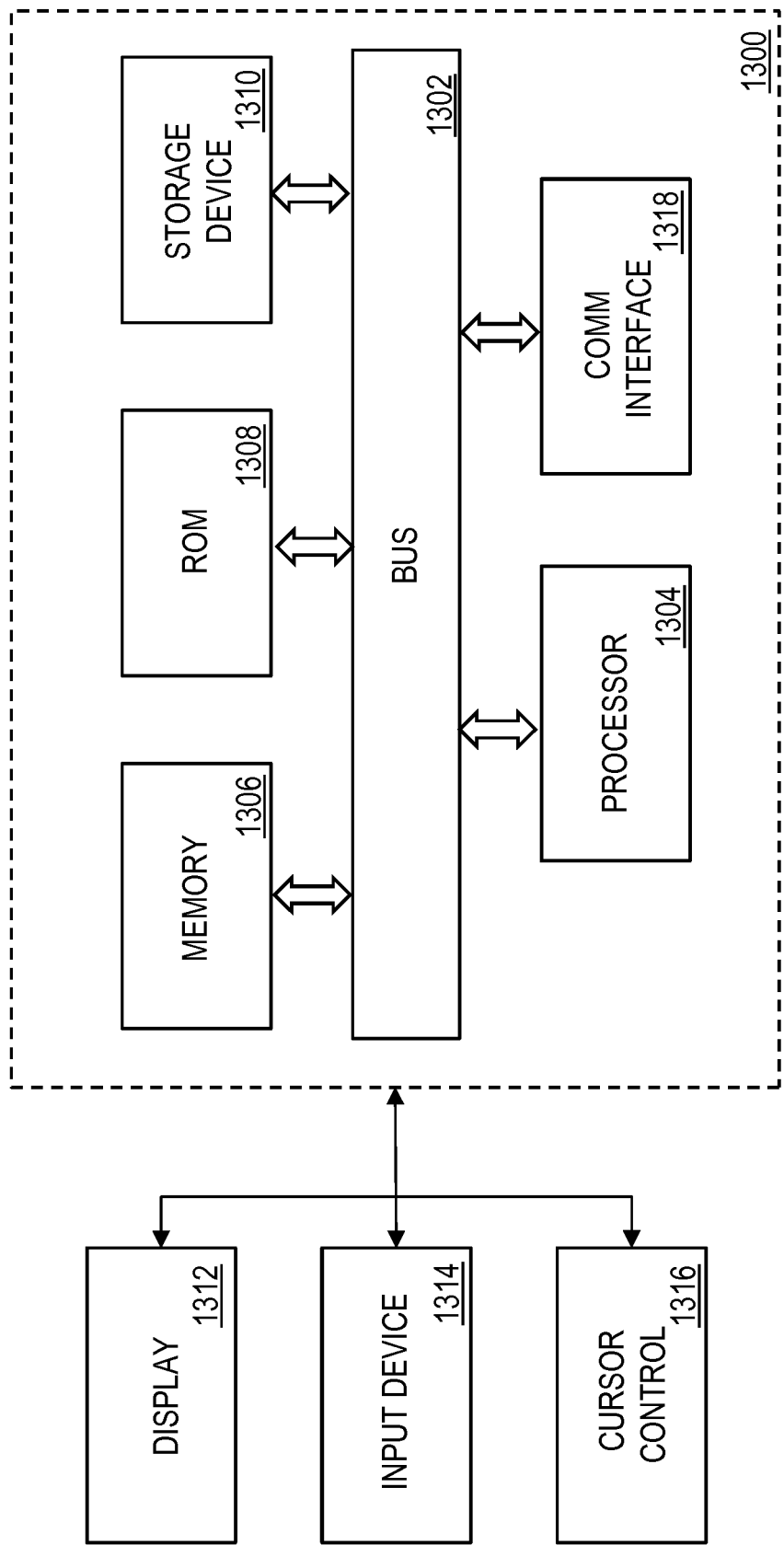
FIG. 1 illustrates a computing system for performing methods for detecting minor variants according to embodiments of the present teachings.

FIG. 1 is a block diagram that illustrates a computer system 1300 that may be employed to carry out processing functionality, according to various embodiments. Instruments to perform experiments may be connected to the computing system 1300. Computing system 1300 can include one or more processors, such as a processor 1304. Processor 1304 can be implemented using a general or special purpose processing engine such as, for example, a microprocessor, controller or other control logic. In this example, processor 1304 is connected to a bus 1302 or other communication medium.

Further, it should be appreciated that a computing system 1300 of FIG. 1 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1300 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 1300 may be configured to connect to one or more servers in a distributed network. Computing system 1300 may receive information or updates from the distributed network. Computing system 1300 may also transmit information to be stored within the distributed network that may be accessed by other clients connected to the distributed network.

Computing system 1300 may include bus 1302 or other communication mechanism for communicating information, and processor 1304 coupled with bus 1302 for processing information.

Computing system 1300 also includes a memory 1306, which can be a random access memory (RAM) or other dynamic memory, coupled to bus 1302 for storing instructions to be executed by processor 1304. Memory 1306 also may be used for storing temporary variables or other intermediate information during execution of instructions to be executed by processor 1304. Computing system 1300 further includes a read only memory (ROM) 1308 or other static storage device coupled to bus 1302 for storing static information and instructions for processor 1304.

Computing system 1300 may also include a storage device 1310, such as a magnetic disk, optical disk, or solid state drive (SSD) is provided and coupled to bus 1302 for storing information and instructions. Storage device 1310 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1310 may include other similar instrumentalities for allowing computer programs or other instructions or data to be loaded into computing system 1300. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1310 to computing system 1300.

Computing system 1300 can also include a communications interface 1318. Communications interface 1318 can be used to allow software and data to be transferred between computing system 1300 and external devices. Examples of communications interface 1318 can include a modem, a network interface (such as an Ethernet or other NIC card), a communications port (such as for example, a USB port, a RS-232C serial port), a PCMCIA slot and card, Bluetooth, etc. Software and data transferred via communications interface 1318 are in the form of signals which can be electronic, electromagnetic, optical, or other signals capable of being received by communications interface 1318. These signals may be transmitted and received by communications interface 1318 via a channel such as a wireless medium, wire or cable, fiber optics, or other communications medium. Some examples of a channel include a phone line, a cellular phone link, an RF link, a network interface, a local or wide area network, and other communications channels.

Computing system 1300 may be coupled via bus 1302 to a display 1312, such as a cathode ray tube (CRT) or liquid crystal display (LCD), for displaying information to a computer user. An input device 1314, including alphanumeric and other keys, is coupled to bus 1302 for communicating information and command selections to processor 1304, for example. An input device may also be a display, such as an LCD display, configured with touchscreen input capabilities. Another type of user input device is cursor control 1316, such as a mouse, a trackball or cursor direction keys for communicating direction information and command selections to processor 1304 and for controlling cursor movement on display 1312. This input device typically has two degrees of freedom in two axes, a first axis (e.g., x) and a second axis (e.g., y), that allows the device to specify positions in a plane. A computing system 1300 provides data processing and provides a level of confidence for such data. Consistent with certain implementations of embodiments of the present teachings, data processing and confidence values are provided by computing system 1300 in response to processor 1304 executing one or more sequences of one or more instructions contained in memory 1306. Such instructions may be read into memory 1306 from another computer-readable medium, such as storage device 1310. Execution of the sequences of instructions contained in memory 1306 causes processor 1304 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1304 for execution. Such instructions, generally referred to as "computer program code" (which may be grouped in the form of computer programs or other groupings), when executed, enable the computing system 1300 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 1310. Volatile media includes dynamic memory, such as memory 1306. Transmission media includes coaxial cables, copper wire, and fiber optics, including the wires that comprise bus 1302.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1304 for execution. For example, the instructions may initially be carried on magnetic disk of a remote computer. The remote computer can load the instructions into its dynamic memory and send the instructions over a telephone line using a modem. A modem local to computing system 1300 can receive the data on the telephone line and use an infra-red transmitter to convert the data to an infra-red signal. An infra-red detector coupled to bus 1302 can receive the data carried in the infra-red signal and place the data on bus 1302. Bus 1302 carries the data to memory 1306, from which processor 1304 retrieves and executes the instructions. The instructions received by memory 1306 may optionally be stored on storage device 1310 either before or after execution by processor 1304.

Figure 2:
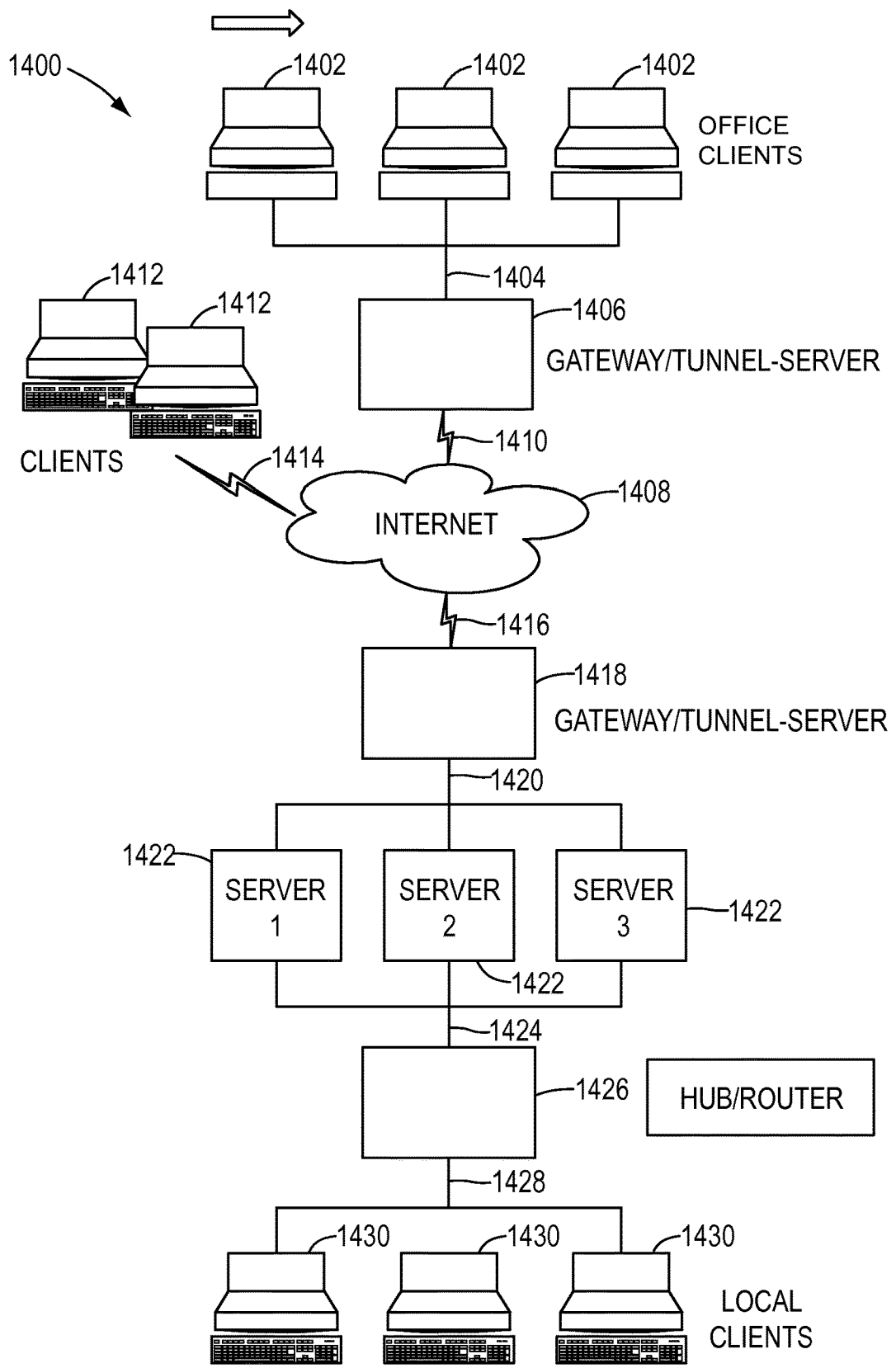
FIG. 2 illustrates a distributed system for performing methods for detecting minor variants according to embodiments of the present teachings.

Some of the elements of a typical Internet network configuration 1400 are shown in FIG. 2, wherein a number of client machines 1402 possibly in a remote local office, are shown connected to a gateway/hub/tunnel-server/etc. 1410 which is itself connected to the internet 1408 via some internet service provider (ISP) connection 1410. Also shown are other possible clients 1412 similarly connected to the internet 1408 via an ISP connection 1414, with these units communicating to possibly an office or central lab, for example, via an ISP connection 1416 to a gateway/tunnel-server 1418 which is connected 1420 to various enterprise application servers 1422 which could be connected through another hub/router 1426 to various local clients 1430. Any of these servers 1422 could function as a development server for the analysis of potential content management and delivery design solutions as described in the present invention, as more fully described below.

As mentioned above, different types of biological data may be presented in a graphical representation display, so that a user may be able visualize the data in a useful way.

Although the present invention has been described with respect to certain embodiments, examples, and applications, it will be apparent to those skilled in the art that various modifications and changes may be made without departing from the invention.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

The teachings herein relate at least in part to biological analysis devices and systems, including, for example, a base calling system for the determination of a DNA sequence. Different types of biological analysis devices and systems can be used for collecting raw sequencing data. These biological analysis devices and systems can include, for example, sequencers. Many of these biological analysis devices and systems utilize labels that are attached to DNA fragments. While sequencing systems may be referenced below, these systems are used for example purposes, as the embodiments described herein may be applied to biological analysis devices and systems in general.

These DNA fragments are formed from a sample and separated according to mobility. In various biological analysis devices and systems, slab gels and polymer filled capillaries are used for the separation and an electric field is used to effect migration of the fragments in these media. Reading of the labels over time produces a signal that is comprised of a trace for each channel where a channel corresponds to a respective label (e.g., a dye). In some systems, additional channels are included that can yield information in additional to the channels corresponding to the nucleotides. This information can be used for better estimating spacing or other parameters that may render sample analysis easier. Such a system is contemplated in U.S. patent application Ser. No. 10/193,776 (publication no. 03-0032042), assigned to the assignee hereof, which is incorporated by reference herein in its entirety.

Capillary Electrophoresis (CE), for example, results in (typically 4) electropherogram sequencing signal traces. The signal traces are proxies indicating the arrival times of DNA amplicon fragments of varying lengths, ending in the DNA "letters" G, A, T, and C, at a measurement location along the capillary tubes in the instrument. For a given "arrival time", the amplitudes of the signal traces corresponding to the amplicon fragments ending in G, A, T, and/or C (the G, A, T, and/or C amplicon fragments) have a shape that very closely approximates a Gaussian distribution. These signals can be provided in, for example, four different traces discussed as follows.

One trace example is a raw electropherogram sequencing signal trace (raw CE signals or raw signals), which can be generated by a CE instrument and corresponds most closely to what is directly measured by the instrument. Longer fragments (i.e. having a greater number of bases) generally arrive later in the raw CE signals. Signals corresponding to amplicon fragments of the same length (i.e. containing the same number of bases), but which end with different letters, generally will have different mobilities and arrive at different times.

Another trace type is a spectrally corrected raw electropherogram sequencing signal trace (spectrally corrected raw signals), which includes raw signals corrected for spectral feed-through. This electrical spectral feed-through occurs because the filters used to derive the signals corresponding to the DNA "letters" G, A, T, and C generally have different peak spectral bins, but nonetheless have spectral bins which overlap with each other. As a result, the electrical signal in one raw signal trace can be fed-though as, and become convolved with, signals in the other raw signal traces. However, knowledge of the spectral shapes of each filter, along with other insights, can be used to de-convolve (spectrally correct) the signals in the raw traces to produce spectrally corrected raw signals.

Another trace type is a mobility corrected electropherogram sequencing signal trace (mobility corrected signals), which include spectrally corrected raw signals corrected for the differences in the mobilities of DNA amplicon fragments of the same lengths (i.e. containing the same number of bases). As a result, the mobility corrected signal traces have corrected arrival times corresponding to amplicon fragments of the same length, based on the expected mobility differences, so that they arrive at about the same time.

Yet another trace example is an analyzed electropherogram sequencing signal trace (analyzed signals), which includes mobility corrected signals that have been re-sampled, and shifted as needed, so that the number of scan points between the arrivals of fragments that differ in length by 1 base number is approximately constant. This number of scan points between the arrivals of fragments that differ in length by 1 base number is typically about 12-16.

Figure 3:
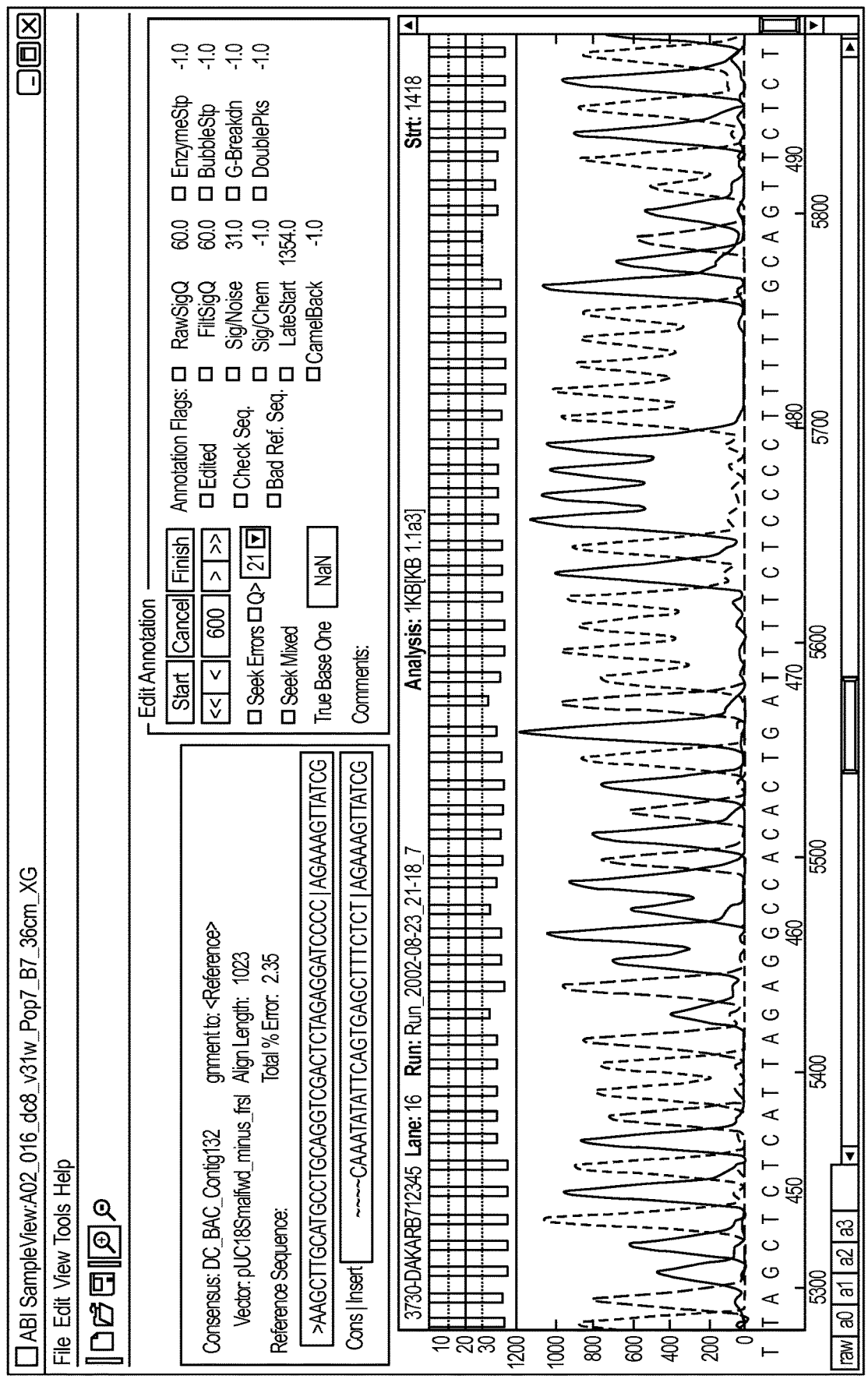
FIG. 3 illustrates electrophoretic traces that can result from the separation of fragments according to embodiments of the present teachings.

FIG. 3 shows data from a typical sequencer. Here four traces are present. Each trace represents a channel. Each channel represents a different label and each label corresponds to a different nucleotide. This data is taken from the middle of a sample run and would be considered by one skilled in the art to be of good quality. Good quality can be assessed by the regularity of the spacing and the distinctness of the peaks. The base calls appear under each peak as the letters A, C, G, and T. Quality values appear above the peaks with a longer bar representing a higher quality value. The lower set of numbers on the x-axis represents the scan number and the higher set represents the base number. The x-axis can also be considered to represent time.

In some embodiments, a model-based peak detection module of a system can use information from the calibration module in detecting peaks. In doing so, the peak detection module can identify clusters of peaks, where clusters can have one or more peaks. The peaks can be distinct or, in the case of poor resolution, the peaks can be smeared together. By using estimates of the signal's parameters, a peak cluster can be resolved into its constituent peaks.

In various embodiments, a peak classification module of a system can classify the peaks detected as belonging to sample-signal or noise space. Some embodiments of the system utilize graph theoretic approaches to perform the classification. In forming the graph, for example, peak characteristics, local sequence characteristics, and/or global signal characteristics can be used to define transition weights between the peaks.

Because of the variability or strength of the noise space, small peaks in the sample-signal space appearing under a main peak in the sample-signal space (those associated with minor variants) can be mistaken as belonging to the noise space. This limitation can be resolved by applying the techniques in the teachings that follow. Different combinations of sequence data can be used such as those provided, for example as follows:

1) A test sample sequenced in either the forward or reverse orientation; this will be referred to as the test sample, single orientation combination;
2) A test sample sequenced in both the forward and reverse orientations; this will be referred to as the test sample, forward and reverse combination;
3) A test sample sequenced in either the forward or reverse orientation combined with a reference sample sequenced in the same orientation as that of the test sample; this will be referred to as the test and reference sample, single orientation combination;
4) A test and reference sample, both sequenced in both the forward and reverse orientations; this will be referred to as the test and reference sample, forward and reverse combination.

The various combinations can provide varying levels of sensitivity and specificity in finding minor variants. Sensitivity and specificity can be further improved by, for example, combining a noise subtraction and suppression method (NSS) with data source combinations (3) or (4). This can also be achieved with data combinations (1) and (2) if a digital reference sample (DRS) or a synthetic digital reference sample (SDRS) is used as a stand-in for the reference sample.

Hence, these teachings below will describe embodiments for detecting minor variants using the data combinations described above, some of which with DRS or SDRS substitutions, and some of which in combination with NSS. The embodiments described herein are for illustrative purposes only and should not be interpreted as placing any limitation on the types of data combinations applicable, the substitution methods for the reference sample, the types of noise subtraction and suppression methods that are applicable, or the combination of any of the above.

Figure 4B:
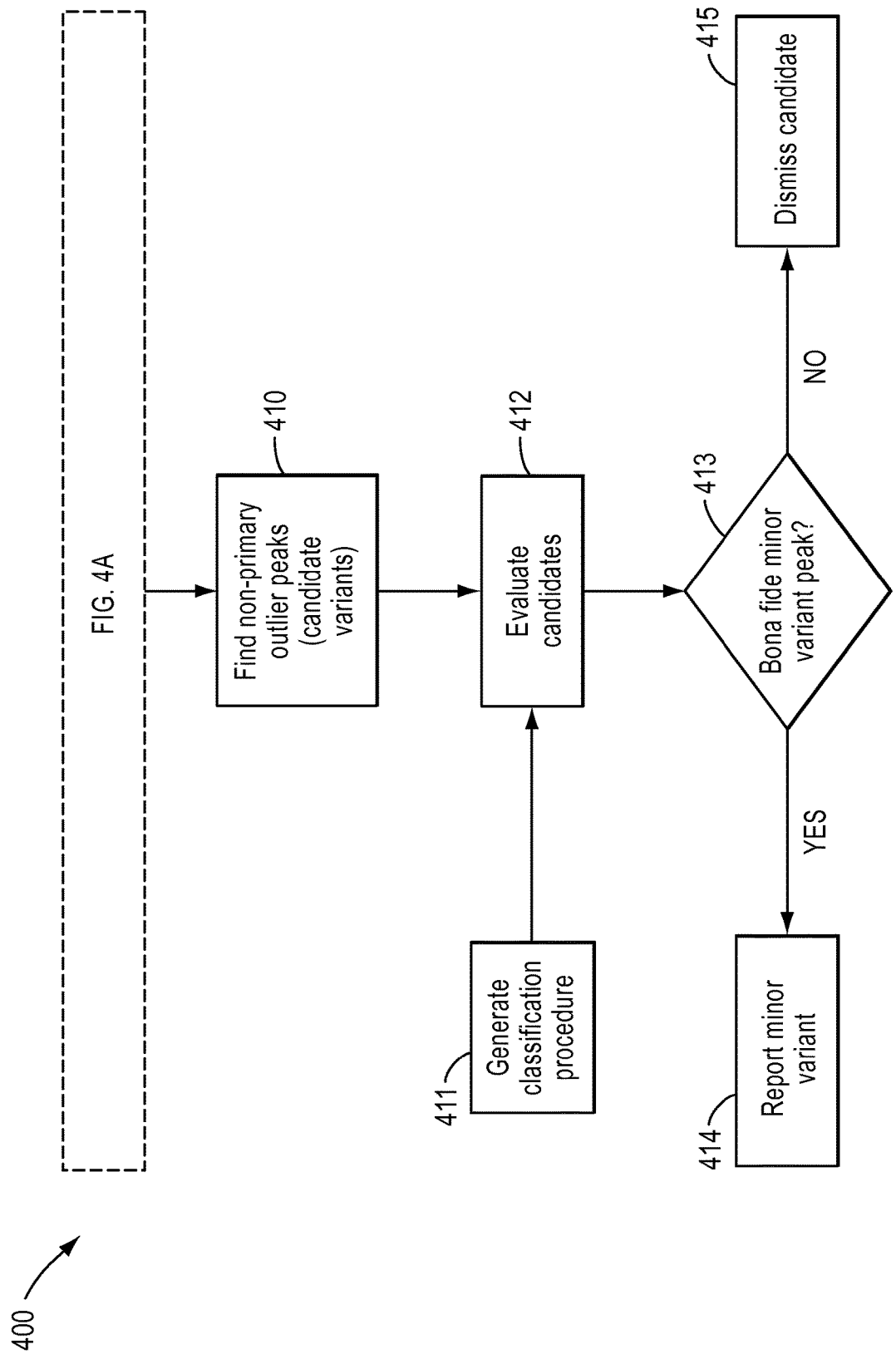

FIGS. 4A-4B illustrate a flowchart depicting an method 400 to determine minor variants using a test sample sequenced in a single orientation (test sample, single orientation combination) according to embodiments described herein. The steps of method 400 may be implemented by a processor 1304, as shown in FIG. 1. Furthermore, instructions for executing the method by processor 1304 may be stored in memory 1306.

With reference to FIG. 4A, in step 401, electropherogram sequencing data from a test sample is collected and provided from the sequencer to processor 1304 for determining minor variants according the embodiments described therein. In step 402, a primary sequence is determined by processor 1304, for example, using instructions stored in memory 1306. The primary sequence may be determined using known software applications such as, for example, KB™ Basecaller sequencing analysis software provided by Applied Biosystems, a signal-processing technology that provides accurate basecalling and quality values (QV) for each base and sample file. Sequencing analysis software such as KB™ Basecaller software by Applied Biosystems™ can also resolve mixed bases (a mixed base is a base position where there are two or more peaks in the sample-signal space; a minor variant at a base position is associated with a peak in the sample-signal space that is smaller than the primary peak) by detecting mixed base positions and assigning IUB (International Union of Biochemistry) codes and QVs to those positions using methods similar to that for pure bases. (However, when the non-primary peak of a minor variant is too small, KB™ Basecaller cannot detect it; hence the need for the teachings herein.)

Returning to FIG. 4A, in step 403, a quality trim (a trim based on QVs) can be conducted to trim low quality data out of the sequence. These trims are generally performed at right and left ends of the sequence. One example of quality trim from the left is to find the base position at which QV is less than 10 and, within 15 base positions to the right of this, all QV's are greater than 10.

In step 404 of FIG. 4A, the data of each of the four dyes corresponding to each of the four possible bases of a genetic sequence is scanned for peaks where there are, for example, a series of points for which there is a sufficiently high maximum flanked by points lower than that maximum. An alternative is to restrict peak finding to an identified target interval which can be, which can be, for a given primary base, within a locus of points defined by the width of the primary base.

In step 405 of FIG. 4A, each non-primary peak is identified and characterized using a one or more of approaches. For each peak, for example, the location of the maximum of the peak and the location of minima that flank the peak are determined. The data between the flanking minima can be fit to a mono-modal function, for example, a Gaussian, that is then used, in part, to characterize the peak, specifically, the location, height, and width of the peak. The data associated with a peak are further processed to compute a number of signal features. signal features can involve, for example, using peak characteristics such as, but not limited to, peak amplitude, peak width, peak location, area under the peak, peak sharpness, peak symmetry/asymmetry, goodness of fit with respect to the mono-modal model (for example, the Gaussian function), height of the minima flanking a peak relative to its amplitude, peak location, and any combinations thereof. Any and all combinations of the above peak characteristics can be applied relative to that of the primary peak under which the non-primary peak in question is found, relative to all primary peaks (for example, average primary peak amplitude across the sequence), and relative to all other non-primary peaks (for example, peak height relative to the median peak height of non-primary peaks across the sequence; example variations are using the cross-dye median or using dye-specific medians). Moreover, any contemplated simple functional transformation can be applied to the above including, for example, exponential, logarithmic, power, sums, products, trigonometric functions, or any other functions that might be used to modify the rate of change or emphasize certain regions of the signal feature's range and/or normalize the statistical distribution of the signal feature.

Step 406 of FIG. 4A illustrates that the functional transformations discussed above may involve non-linear parameters that can be optimized to maximize the ability to distinguish sample-signal space non-primary peaks (minor variant peaks) from noise space non-primary peaks. The optimization can be done by using, for example, one or more of global optimization, local optimization, and classification-driven feature selection techniques. Any of these techniques can be stored in memory 1306 and implemented via processor 1304. Some global optimization examples include, but are not limited to, swarm-theory based algorithms, genetic algorithms, simulated annealing, and any other example that has established and effective means to search for parameter values that can maximize the accuracy of classification given a set of data for which class membership is known. For local optimization, for each choice of non-linear parameter values made by a global optimization algorithm, values for linear parameters can be determined using fast linear methods such as, for example, linear discriminant functions. In classification-driven feature selection, for each discriminant function, for example, all possible combinations of a feature set can be explored to find a combination that achieves the best balance between high classification accuracy and the number of input features required. Optimum parameter values can be included in memory 1306.

Referring now to FIG. 4B, which continues the workflow introduced in FIG. 4A, in step 410, the sequencer, via processor 1304 using instructions that can be stored in memory 1306, statistically analyzes one or more of the signal features for non-primary peaks to identify outliers. These outliers become candidate minor variant peaks.

In step 412 of FIG. 4B, the sequencer, via processor 1304 using instructions that can be stored in memory 1306, evaluates each candidate minor variant peak by a classification procedure to decide whether or not the candidate is a bona fide minor variant peak; step 413 represents this final decision. Step 411 represents the process of creating the classification procedure used in step 412 to evaluate each candidate minor variant peak. The classification procedure can operate on one or more signal features. Any suitable classification procedure that can make a binary decision can be applied. A few examples of binary classifiers include, but are not limited to, discriminant functions, artificial neural networks, and a logistic decision tree, and any other example that has established methods to generate the classification functions using data for which class membership is known. Prior to applying the classifier procedure in step 412, each individual signal feature can be set to classify cases where, based on the signal feature alone, a candidate minor variant peak can be clearly called a bona fide minor variant peak or a non-variant peak. This example of an additional classification step can be referred to as the Single-Variate Clear Cut Classification procedure (SVCCC). Parameter values which define the classification procedure can be included in memory 1306 and executed by processor 1304.

Figure 5A:
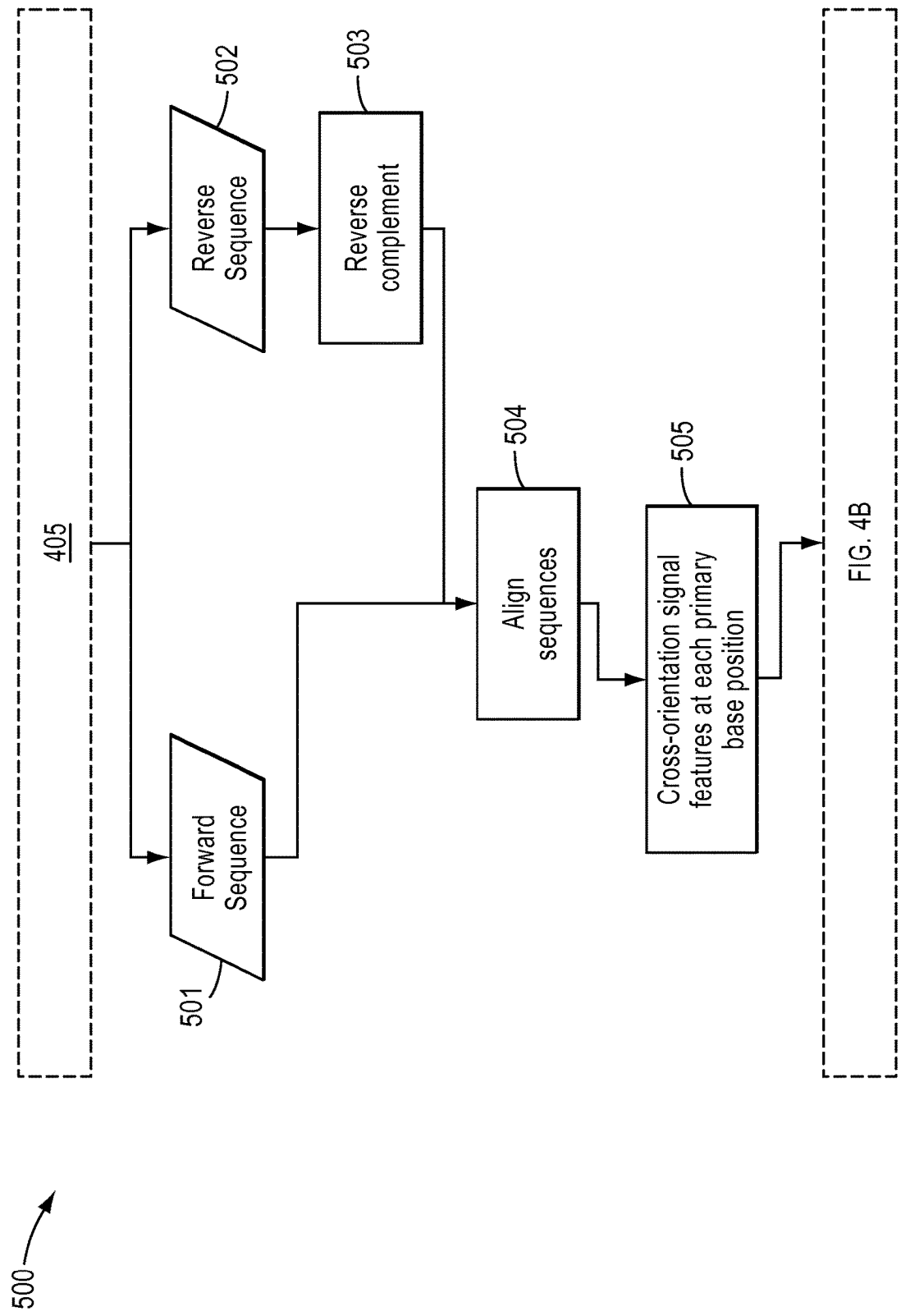
FIGS. 5A-5C illustrate another workflow for determining minor variants according to embodiments of the present teachings.
Figure 5B:
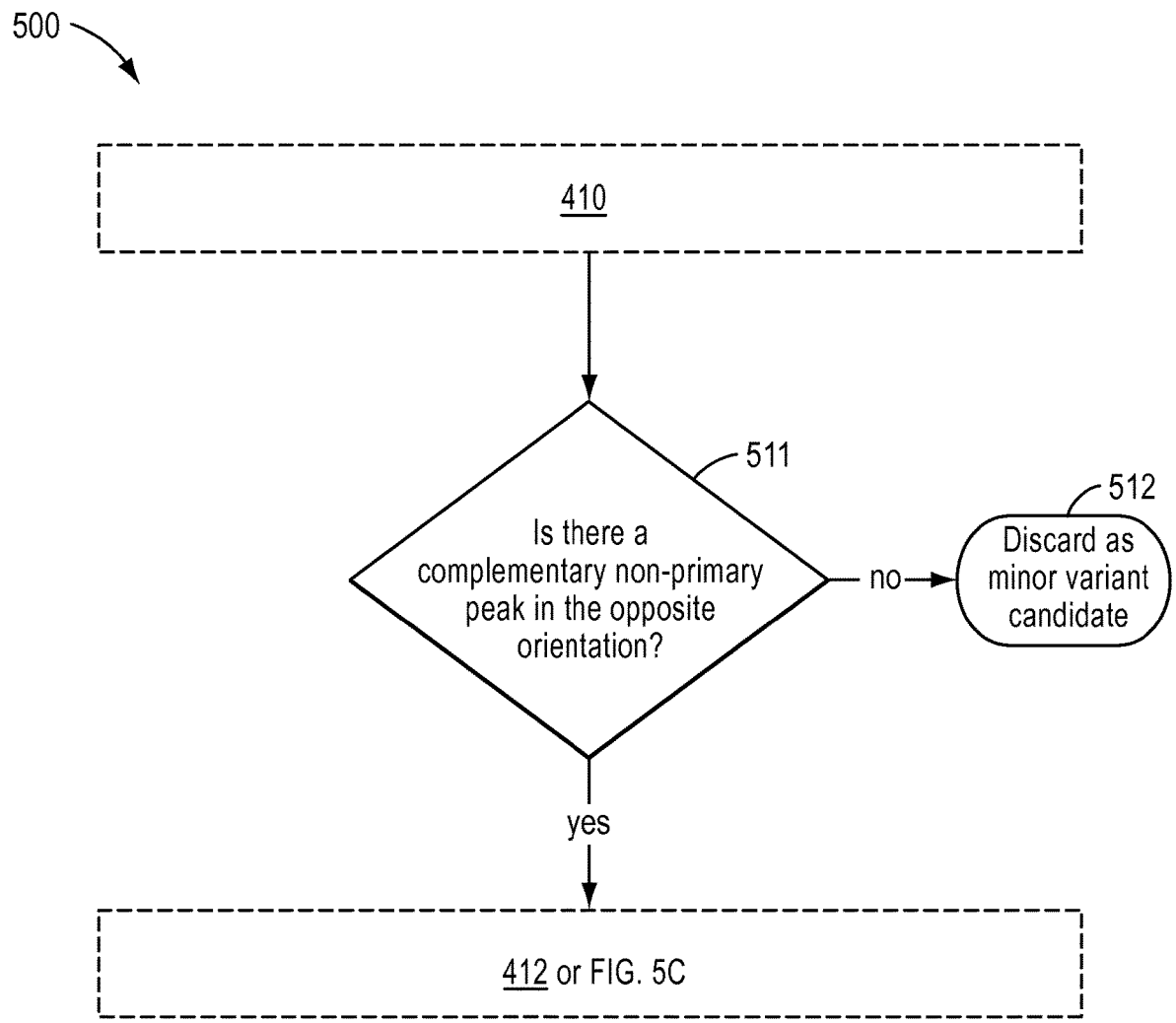
Figure 5C:
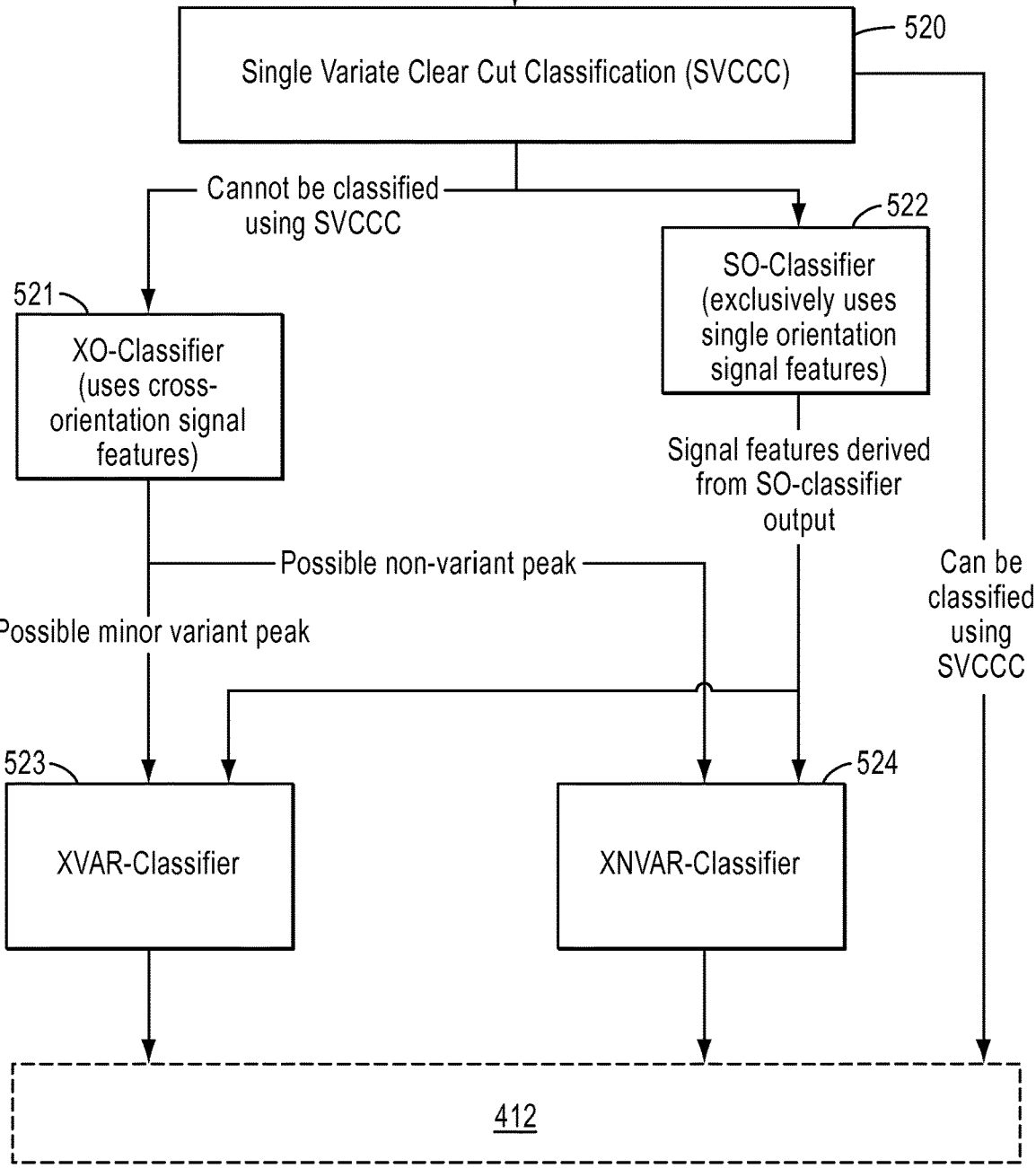

In alternative embodiments to that described in FIGS. 4A-4B, FIGS. 5A-5C illustrate flow charts that modify method 400 described in FIGS. 4A-4B. FIGS. 5A-5C depict a method 500 to determine minor variants using a test sample sequenced in two orientations, both forward and reverse orientations (test sample, forward and reverse combination). With these modifications the steps of method 500 may be implemented by a processor 1304, as shown in FIG. 1. Furthermore, instructions for executing the method by processor 1304 may be stored in memory 1306.

In this embodiment, each sequence orientation is processed through the steps described above and illustrated in both FIGS. 4A and 4B.

Step 405 of FIG. 4A is modified as described below and illustrated in FIG. 5A. In addition to the signal features described above in step 405 in method 400 (for the test sample, single orientation combination), cross-orientation features can be used after aligning the primary base sequences between the two orientations (see steps 501, 502 and 503), as illustrated in step 504 of FIG. 5A. For example, each primary base of the forward sample can be matched with the same primary base in the reverse sample after reverse-complementing the reverse sequence, as illustrated in step 503 FIG. 5A. To execute reverse complementing, one must reverse the order of the sequence and replace each base with its complement, the complementary pairs being A/T and G/C. Any of the signal features described above under step 405 of method 400 can be compared between forward and reverse orientations such as, for example, taking the ratio between the feature values, or the maximum or the minimum divided by the maximum across the two orientations. These cross-orientation signal features can be transformed by any simple functional transformation such as for example but not limited to, exponential, logarithmic, power, sums, products, trigonometric functions, and any other contemplated functions that might be used to modify the rate of change or emphasize certain regions of the signal feature's range and/or normalize the statistical distribution of the signal feature.

Step 410 of FIG. 4B is modified as described below and illustrated in FIG. 5B. In addition to using statistical analysis to find outliers described under method 400, steps 511 and 512 illustrate a decision point where the sequencer, using processor 1304, evaluates and considers a non-primary peak a candidate minor variant peak when it is confirmed by a complementary non-primary peak in the opposite orientation. For example, a non-primary peak associated with the G base in the forward orientation would have a non-primary peak associated with the C base at the corresponding base position in the reverse orientation to be considered a candidate minor variant peak.

Step 411 of FIG. 4B is modified as described below and illustrated in FIG. 5C. Instead of using a single classification function of step 412 or the SVCCC procedure followed by a single classification function described under step 412 of method 400, an alternative to the method described in FIG. 4B step 412 is illustrated in FIG. 5C. In this embodiment, the classification procedure of step 411 is modified to include the SVCCC procedure (step 520 of FIG. 5C), followed by an initial classifier, classifier XO of step 521, that can be based on cross-orientation signal features that makes an initial decision on whether or not a peak is a bona fide minor variant peak, followed by two classifiers, XVAR and XNVAR shown as steps 523 and 524, that can override the decisions of the XO classifier. In addition to the single orientation and cross-orientation signal features shown in steps 520 and 521, classifiers XVAR and XNVAR can accept signal features, SO-output signal features, which can be derived from a classifier based on single-orientation signal features (see the SO classifier of step 522). SO-output signal features can include, but are not limited to, the probability density ratio between a minor variant peak and a non-variant peak based on an empirical statistical distribution model of the output of the SO classifier or a parameterized model such as one that assumes SO-output is normally distributed for each of the two classes; the sum of forward and reverse orientation SO-outputs; and the maximum or minimum of forward and reverse orientation SO-outputs. The SO-output signal features can be can be transformed by any simple functional transformation such as, for example, exponential, logarithmic, power, sums, products, trigonometric functions, and any other functions that might be used to modify the rate of change or emphasize certain regions of the signal feature's range and/or normalize the statistical distribution of the signal feature. Parameter values which define the alternative classification procedure of FIG. 5C can be included in memory 1306 and executed by processor 1304.

In another alternative embodiment to that described in FIGS. 4A-4B, FIG. 6 illustrates a flow chart that modifies method 400 described in FIGS. 4A-4B. FIG. 6 illustrates a method 600 to determine minor variants using a test sample and a reference sample sequenced in the same orientation (test and reference sample, single orientation combination). With these modifications the steps of method 600 may be implemented by a processor 1304, as shown in FIG. 1. Furthermore, instructions for executing the method by processor 1304 may be stored in memory 1306.

In this embodiment, each of the two samples (test and reference) is processed through the steps described above and illustrated in both FIGS. 4A and 4B.

Step 405 of FIG. 4A is modified for method 600 as described below and illustrated in FIG. 6. In addition to the signal features described above in step 405 in method 400 (for the test sample, single orientation combination), cross-sample features can be used, as illustrated in step 604, after aligning the primary base sequences between the samples (see steps 601 and 602) as illustrated in step 603 of FIG. 6. For example, to the degree possible, each primary base of the test sample is matched with the same primary base in the reference sample. Any of the signal features described above can be compared between test and reference samples such as, for example but not limited to, taking the ratio between the feature values or the difference between the feature values. These cross-sample signal features can be transformed by any simple functional transformation such as, for example but not limited to, exponential, logarithmic, power, sums, products, trigonometric functions, and any other contemplated function that might be used to modify the rate of change or emphasize certain regions of the signal feature's range and/or normalize the statistical distribution of the signal feature.

As described above, step 410 of FIG. 4B provides that one or more of the signal features for non-primary peaks can be statistically analyzed to identify outliers. These outliers then become candidate minor variant peaks. For exemplary method 600, these signal features include those derived from the test sample alone as well as those signal features that compare the test with the reference sample. Signal features derived from the reference sample alone are not used for the identification of outliers.

In another alternative embodiment to that described in FIGS. 4A-4B, method 400 can be modified to provide a method for determining minor variants using a test sample and a reference sample sequenced in two orientations, both forward and reverse orientations (test and reference sample, forward and reverse combination). The modifications to method 400 to provide the test and reference sample, forward and reverse combination method described herein, may be implemented by a processor 1304, as shown in FIG. 1. Furthermore, instructions for executing the method by processor 1304 may be stored in memory 1306.

The test and reference sample, forward and reverse combination method is implemented by integrating method 400 with modifications described in methods 500 and 600 described above and illustrated in FIGS. 4A to 4B, 5A to 5C, and 6 for a test and reference sample with both forward and reverse sequences analyzed. Application of the above steps with these sequences results in examining the data for minor variants only within the common intersection between all four sources of data (i.e., test forward, test reverse, reference forward, reference reverse).

Figure 7A:
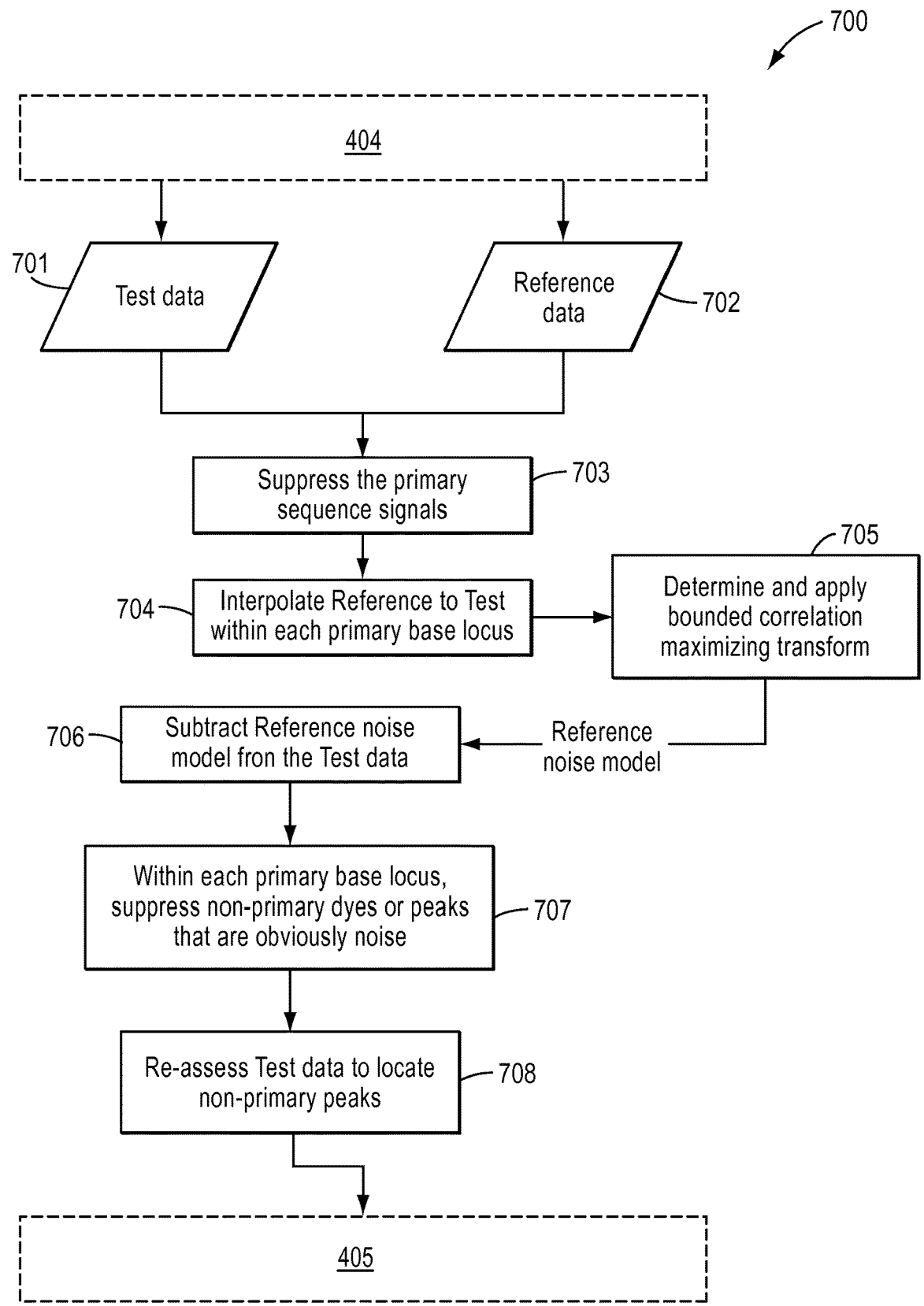
FIG. 7A illustrates a workflow for noise subtraction and suppression according to embodiments of the present teachings.

FIG. 7A is a flowchart depicting a method 700 for improving the sensitivity and specificity of minor variant determination. The steps of method 700 may be implemented by a processor 1304, as shown in FIG. 1. Furthermore, instructions for executing the method by processor 1304 may be stored in memory 1306. Though improving sensitivity and specificity is a feature desirable to any method for minor variant determination, method 700 is applied to minor variant determination methods discussed above where both test and reference samples are sequenced, either in the same direction or in both forward and reverse directions.

Figure 7B:
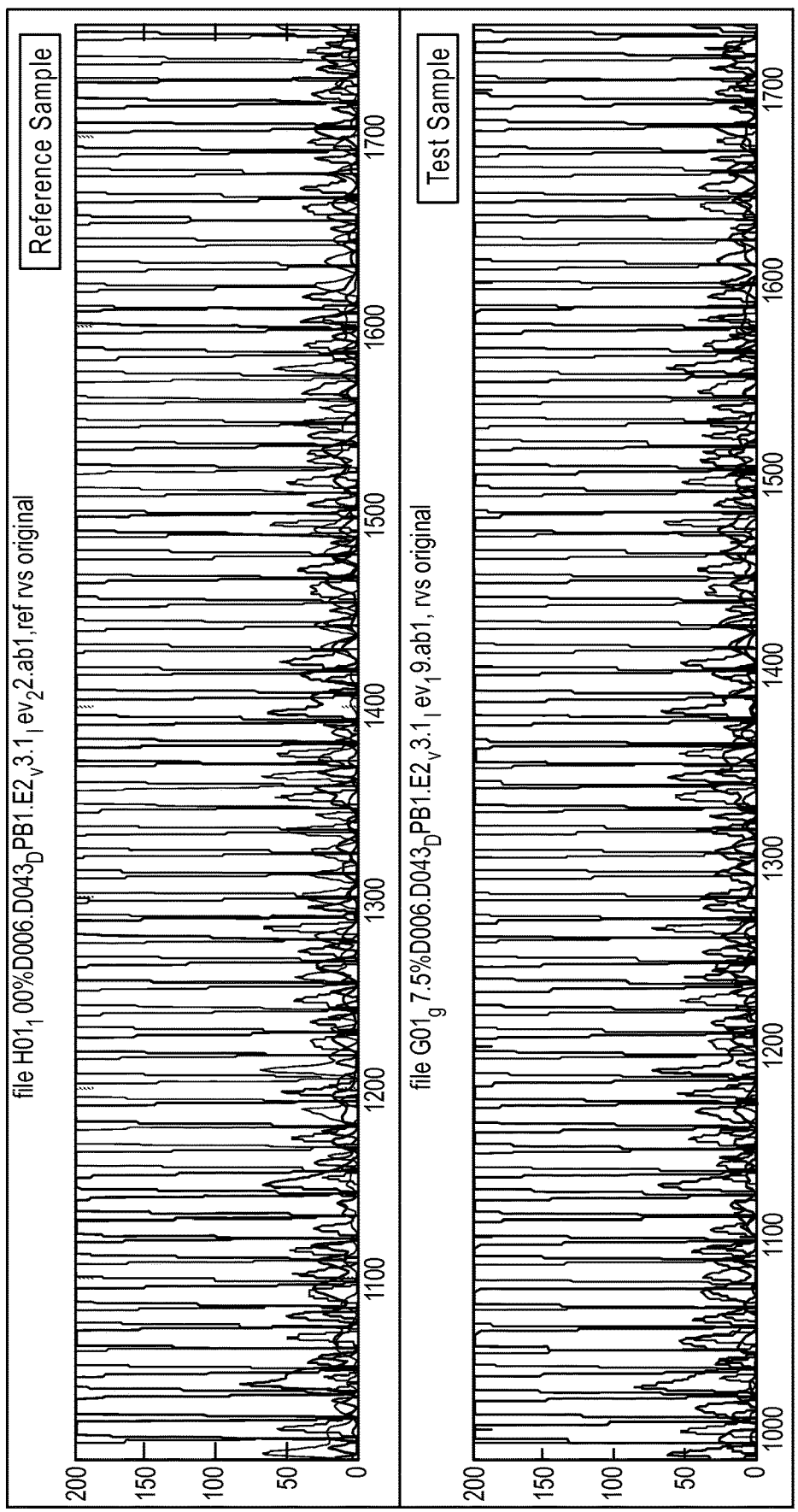
FIGS. 7B and 7C illustrate electropherogram data for test samples, reference samples, and test samples after application of noise subtraction and suppression.

A reference sample can be used to minimize noise in the test sample prior to analyzing non-primary peaks to detect and report minor variants. The dominant component of the noise underlying, for example, capillary electrophoresis Sanger sequencing signals that have been analyzed by a CE sequencer's primary data analysis software (such as, for example, KB™ Basecaller), appears to be determined by the primary base sequence and configuration of the system used to sequence the genetic material. For example, if two independent samples share the same primary sequence, the underlying noise is observed to be very similar between the two. FIG. 7B illustrates such a situation. The panels illustrated in FIG. 7B show the bottom 200 relative fluorescence units (RFU) data underlying electropherograms of reference and test samples. By comparing upper and lower panels, it is apparent that the signals look similar (note primary peaks around 1000 RFUs for these samples). Moreover, the noise subtraction and suppression method (NSS), method 700 discussed below, does not require an understanding of the details of the relationship between primary sequence, sequencing system configuration, and noise to work.

In an embodiment, a sequencer, via processor 1304 using instructions that can be stored in memory 1306, processes a test sample's electropherogram to minimize the noise in the electropherogram by building a model of the noise from a reference sample's electropherogram and subtracting that model from the test sample's electropherogram. The sequencer can then, as illustrated in FIGS. 4 through 6 and described above, examine non-primary peaks of the de-noised electropherogram to find peaks associated with minor variants.

In steps 701 and 702 of FIG. 7A, the sequencer, via processor 1304 using instructions that can be stored in memory 1306, acquires test and reference sample sequence data processed up through step 404 of FIG. 4A for further processing.

In step 703, the sequencer, via processor 1304 using instructions that can be stored in memory 1306, removes the primary sequence signals from the test and reference electropherograms by, at each primary base position, setting the values of the dye corresponding to the primary sequence base to zero between the flanking minima of the primary peak. This operation leaves two electropherograms, test and reference sample electropherograms, composed of only non-primary data.

In steps 704 and 705, the sequencer, via processor 1304 using instructions that can be stored in memory 1306, takes steps to maximize the match between the test and reference non-primary data using, for example, interpolation within the locus of each primary base to match widths and scaling and offset optimization to maximize the correlation between the test and reference non-primary data (minimize the difference between the two). The scaling and offset factors can be constrained to prevent the destruction of true differences between the test and reference non-primary data. This operation can be termed a bounded correlation maximizing transform that applies dye-specific range-limited scale and offset adjustments to match reference to test non-primary signals over a number of primary loci that are centered on the primary base position of interest. The result is a noise model of the non-primary signals underlying the reference electropherogram that has been adjusted to match that underlying the test electropherogram.

Figure 7C:
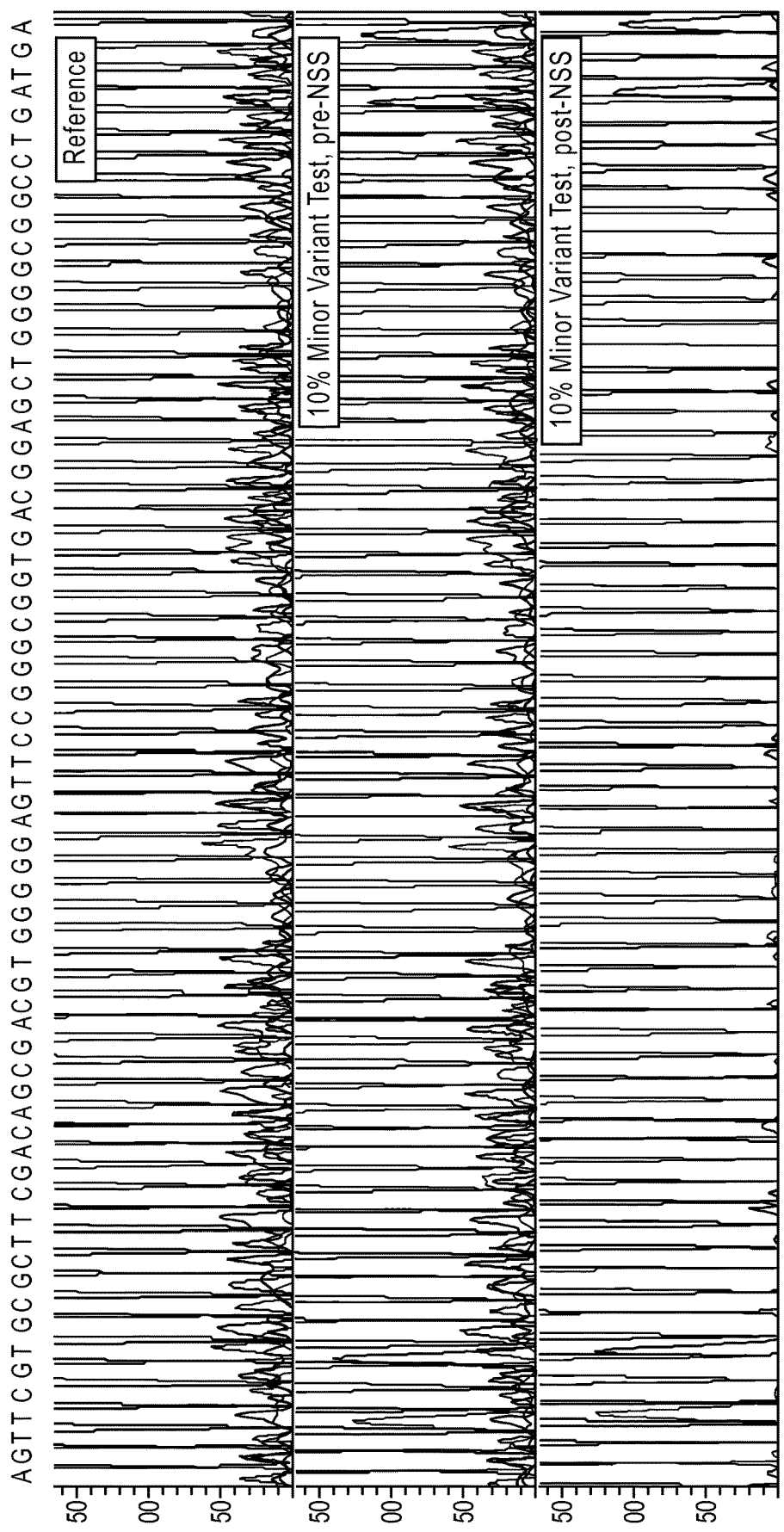

In step 706, the sequencer, via processor 1304 using instructions that can be stored in memory 1306, subtracts the noise model from the test electropherogram. This process can leave signal artifacts in the data; for example, peaks characterized by extreme sharpness or needle-like appearance. Non-primary dye data may be non-zero yet may not contain any peak within the locus of a primary base. In step 707, the sequencer can resolve both of these situations by suppressing the non-primary dye, for example, by setting the dye values to zero within an appropriate range. FIG. 7C shows the results of method 700 applied to the example in FIG. 7B. In particular, FIG. 7C shows, for a forward trace on a 10% minor variant test sample, noise levels before and after applying NSS. The noise in the control is very similar to the rare variant sample and that by minimizing the noise, overall noise level can be reduced, for example, by three to four times.

In step 708 of FIG. 7A, the test data, now modified by NSS, is re-assessed to detect and characterize non-primary peaks. At this point, the reference data is no longer needed and subsequent processing is applied to the NSS-modified test data. For method 600 (test and reference sample, single orientation combination), the modification by method 700 is complete at this point and the remaining steps of method 600 are applied to the modified test data. For the test and reference sample, forward and reverse combination method discussed above, the modification by method 700 is applied to forward and reverse orientation data, with the modified test data for both the forward and reverse orientations moved through the remaining steps of the test and reference sample, forward and reverse combination method.

In the embodiment described above and illustrated by FIGS. 7A-7C above, NSS is shown as applied to embodiments where test and reference samples are analyzed. In yet another embodiment, illustrated by FIG. 8, method 700 can be modified to apply to methods 400 and 500, described above and illustrated by FIGS. 4A-4B and 5A-5C, where no reference sample is considered. First, step 702 of FIG. 7A is inapplicable without a reference sample. Next, as provided by method 800 of FIG. 8 and described below, in place of the reference sample, a digital reference sample can be used whereby the digital reference sample is, for example, constructed from previously processed samples that have the same primary sequence as the test sample or from a collection of test samples from the same sequence processing run when all the test samples of that run interrogate the same region of the genome (and, hence, share the same primary sequence). Instructions for executing method 800 by processor 1304 may be stored in memory 1306.

Figure 8:
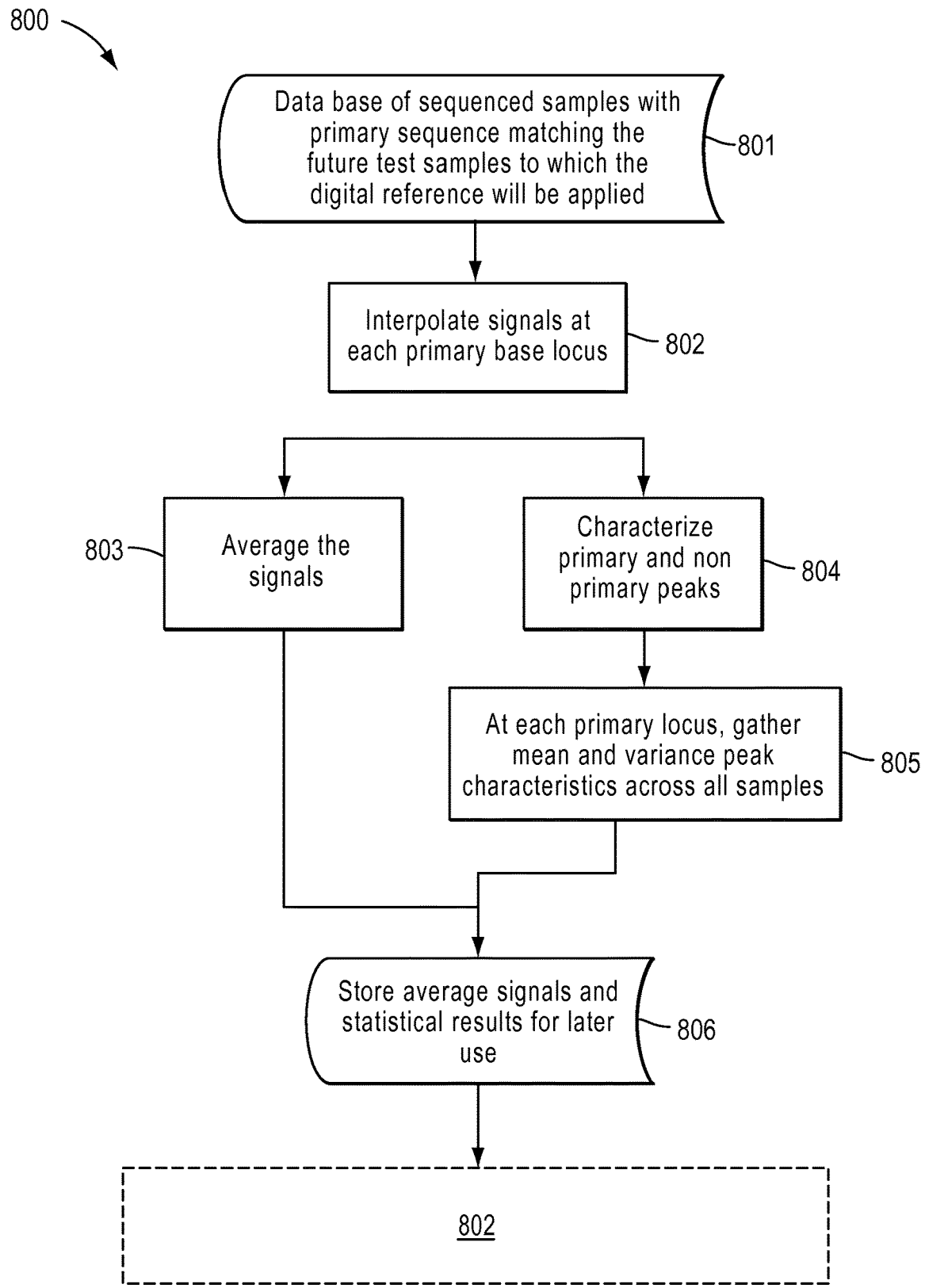
FIG. 8 illustrates a workflow for generating a digital reference sample according to embodiments of the present teachings.

FIG. 8, illustrates the digital reference construction process using, as provided in step 801, a database of sequenced data that have the same primary sequence as the test samples to be analyzed or a database consisting of sequence data of test samples from the same sequence processing run that share the same primary sequence.

In step 802 of FIG. 8, the sequencer, via processor 1304 using instructions that can be stored in memory 1306, ensures that the width spanned by each primary base matches up across all the samples in the database. This can be done by using, for example, an interpolation function such as, for example, a cubic spline.

In step 803 of FIG. 8, the sequencer, via processor 1304 using instructions that can be stored in memory 1306, generates an average electropherogram where the noise that is not statistically correlated between the samples in the database can be reduced by a factor of the square root of N where N is the number of samples in the database. In the case where test samples are used in the database, the underlying assumption is that the location of minor variants varies across the test samples; this being the case, the averaging process can severely diminish their contribution to the final signal average. The averaging process leads to a cleaner estimate of the noise in the electropherogram that is correlated to the primary sequence. The average electropherogram produced in step 803 is stored for use in step 806 as a stand-in for a reference sample in step 702 of FIG. 7A.

Steps 804 and 805 provide statistics that can help in subsequent processing to distinguish between non-primary peaks that are associated with minor variants from those that are not. For example, after NSS using the digital reference, if a remaining non-primary peak rises above the baseline value of zero by, for example, no more than two standard deviations as measured in step 805, it can be considered noise. Any remaining non-primary peak greater than, for example, two standard deviations can be considered a candidate for a minor variant peak. Steps 804 and 805, and stored average signals and statistical results in step 806, can therefore be used in addition to or in place of step 410 of method 400 to locate candidate minor variants.

Figure 9A:
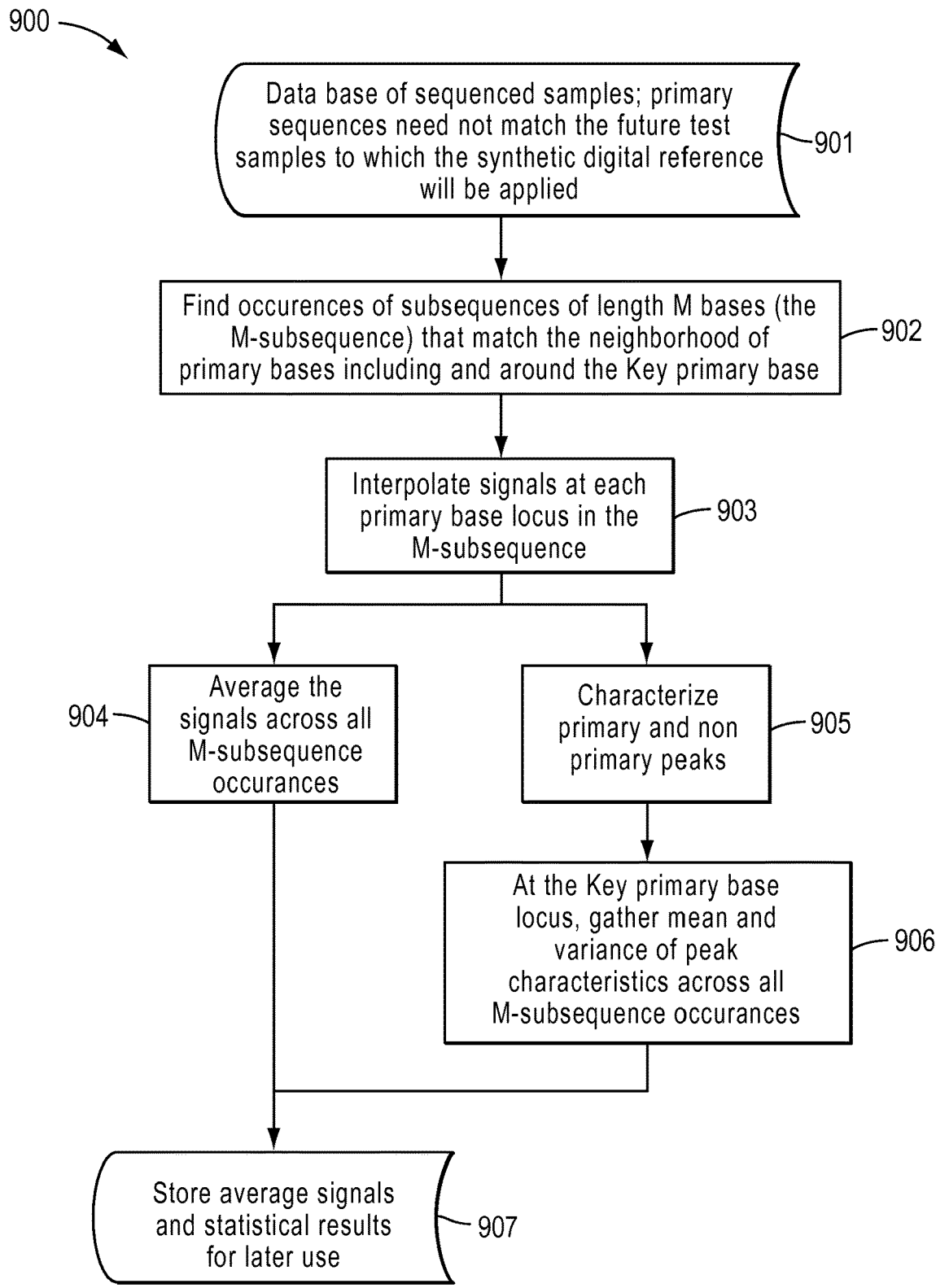
FIGS. 9A and 9C illustrate another workflow for generating a digital reference sample according to embodiments of the present teachings.
Figure 9B:
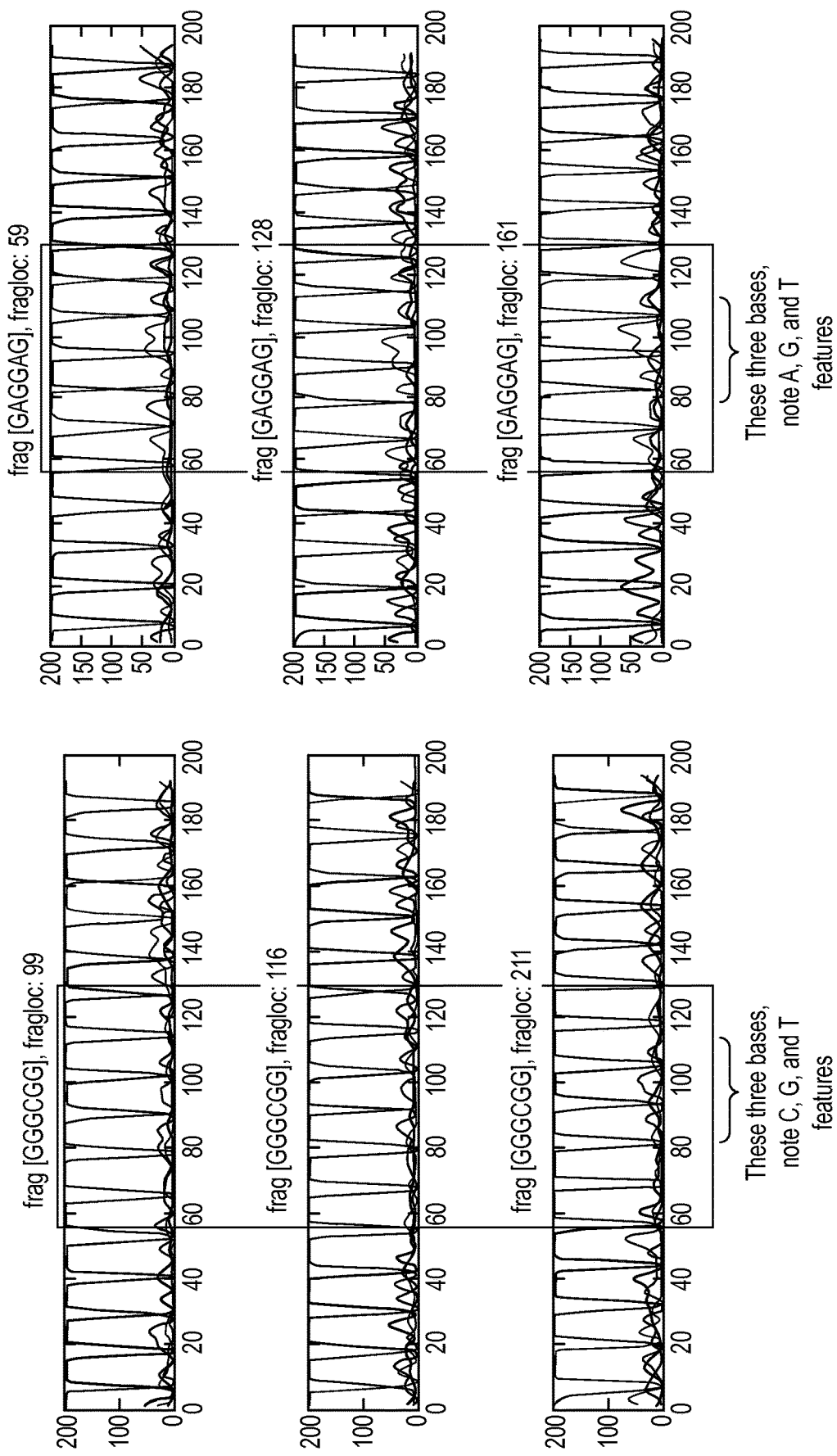
FIG. 9B illustrates supporting sequencing data.
Figure 9C:
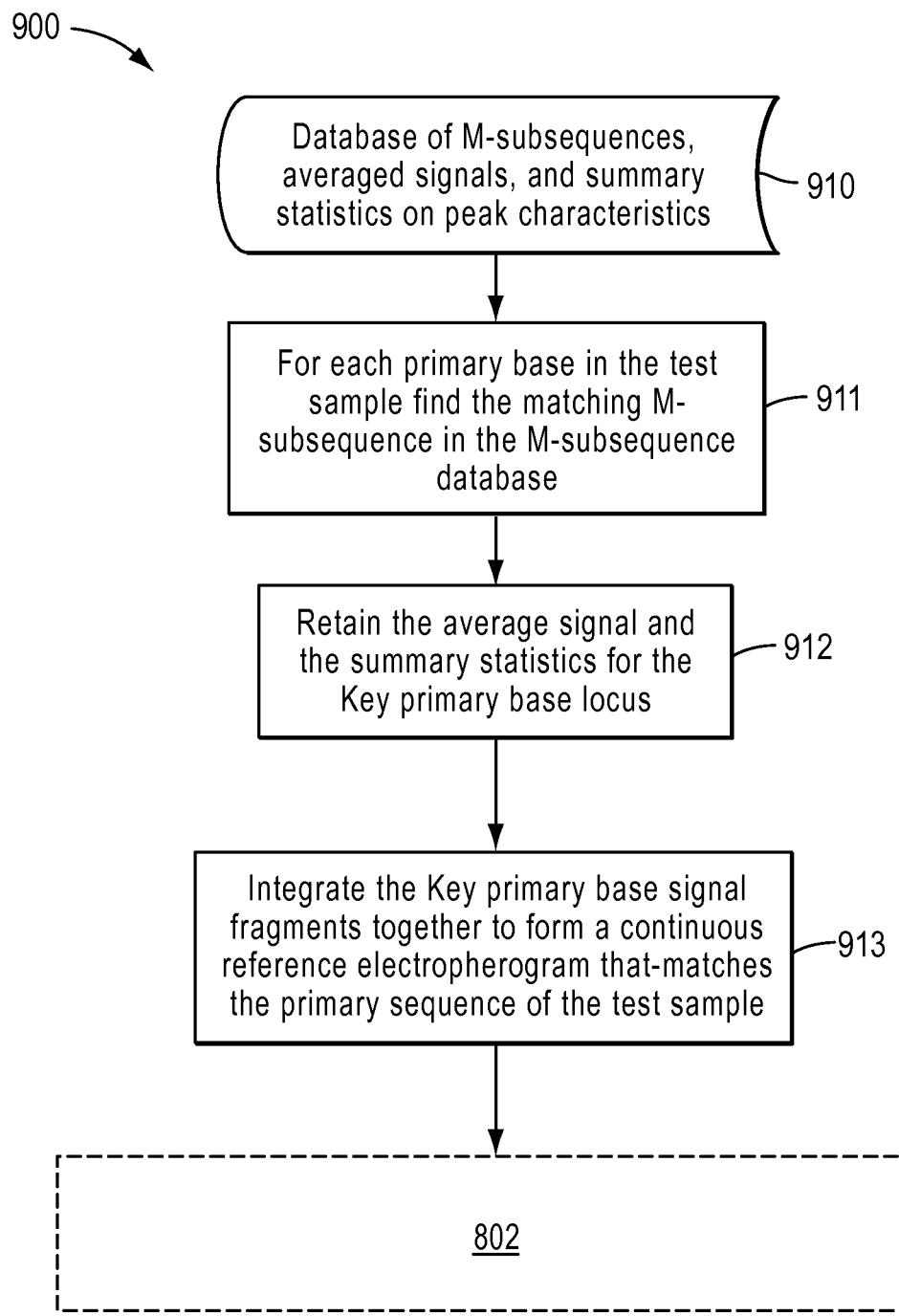

Alternative to the above method 800, which requires a database of sequencing results for which the primary sequence matches that of test samples to be analyzed using the digital reference, FIGS. 9A-9C describe a method 900 that can generate a digital reference using a database of samples that do not necessarily match the primary sequence of the test samples. Method 900 synthesizes the digital reference from many short subsequences of data that span, for example, 7 bases and match a subsequence of the same length within the primary sequence of the test sample (see step 901 in FIG. 9A). Instructions for executing processes describe in FIGS. 9A and 9C by processor 1304 may be stored in memory 1306.

FIG. 9A shows the portion of method 900 concerned with generating a collection of results that can be used to synthesize a digital reference for any test sample. In step 902 of FIG. 9A, the sequencer, via processor 1304 using instructions that can be stored in memory 1306, locates all occurrences of subsequences of length M bases (the M-subsequence) that match the neighborhood of primary bases; $4^M$ unique subsequences are located within the database since all possible subsequences M-bases long must be covered to enable synthesizing a digital reference to match any test sample. Using the example M=6, 4096 unique subsequences, and, ideally, many replicates of these subsequences, must be found in the database (see step 901). One of the bases, the Key primary base, is a position within each subsequence, for example, the fourth base from the leftmost base, from which results are applied to synthesize the digital reference. Hence, each primary position in the digital reference to be synthesized generally has a slightly different subsequence.

FIG. 9B shows sequencing data that support method 900. Three independent samples for each of two unique 6-base subsequences are shown. Three occurrences for each were found within a single sequencing run covering approximately 325 bases. It can be observed that the signals for the fourth base from the left, the Key primary base, are very similar across the three independent samples. In these results, it appears that the Key primary base can be considered to be base 4 or 5 within the 6-base subsequence.

The final results, used to synthesize the digital reference, are an average over all replicates of an M-subsequences found in the database having the same base value at the Key primary base position. Steps 903 to 906 function similarly to steps 802 to 805 of FIG. 8 described above except that, in method 900, steps 903 to 906 are applied to many short subsequences of data and each subsequence generally contributes a single primary base of results to the synthesis. Hence, step 907 is a database that consists of a large number of subsequence results, each of which is used for a single base in the subsequence, the Key primary base.

FIG. 9C shows the portion of method 900 concerned with synthesizing a digital reference for a specific test sample. In step 911, the sequencer, via processor 1304 using instructions that can be stored in memory 1306, searches the database of M-subsequences to find a matching M-subsequence for each primary base of the test sample. In step 912, the sequencer extracts the results for the Key primary base, and integrates the Key primary base signal fragments for each base position of the test sample together in step 913, to form a complete digital reference electropherogram that matches the primary sequence of the test sample. This digital reference can be used as a stand-in for a reference sample in step 702 of FIG. 7A. The summary statistics can be used as described for method 800, steps 804 and 805.

Various embodiments of the present invention have been described above. It should be understood that these embodiments have been presented by way of example only, and not limitation. It will be understood by those skilled in the relevant art that various changes in form and detail of the embodiments described above may be made without departing from the spirit and scope of the present invention as defined in the claims. Thus, the breadth and scope of the present invention should not be limited by any of the above-described exemplary embodiments, but should be defined only in accordance with the following claims and their equivalents.

What is claimed is:

1. A computer-implemented method for determining minor variants of genetic material, the method comprising:
    performing, by an electrophoresis sequencer, electropherogram sequencing of a test sample in both a forward orientation and a reverse orientation, wherein the test sample includes the genetic material, and
    using one or more processors with instructions stored in memory to perform processing comprising:
        receiving electropherogram sequence data of the test sample in both the forward orientation and the reverse orientation,
        identifying any non-primary peaks in the electropherogram sequence data of the test sample in both the forward orientation and the reverse orientation,
        obtaining identified variant candidates by, for each of a plurality of non-primary peaks in the forward orientation, confirming whether a non-primary peak is present at a complementary location in the reverse orientation, and determining a non-primary peak in the forward orientation to indicate a candidate variant if it is confirmed at the complementary location in the reversed orientation,
        evaluating at least one peak characteristic of each of the identified variant candidates, and
        classifying variant candidates as bona fide variants based on the evaluation of peak characteristics.

2. The computer-implemented method of claim 1, further comprising:
    receiving electropherogram sequence data from a reference sample.

3. The computer-implemented method of claim 1, wherein the obtaining identified variant candidates comprises:

characterizing identified non-primary peaks in both the forward orientation and the reverse orientations using at least one signal feature associated with the identified non-primary peaks in both the forward orientation and the reverse orientations, wherein the at least one signal feature includes features used to compare the characteristics of one or more of the non-primary peaks to characteristics of one or more primary peaks.

4. The computer-implemented method of claim 1, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature includes features used to compare the characteristics of one or more of the non-primary peaks to characteristics of at least one primary peak under which at least one non-primary peak is positioned.

5. The computer-implemented method of claim 1, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature is associated with the identified non-primary peaks of the test sample, the method further comprising:
identifying any non-primary peaks in electropherogram sequence data of a reference sample,
characterizing identified non-primary peaks of the reference sample using at least one signal feature associated with the identified non-primary peaks of the reference sample, and
analyzing the at least one signal feature associated with the identified non-primary peaks of the test sample and the at least one signal feature associated with the identified non-primary peaks of the reference sample to identify variant candidates in the test sample.

6. The computer-implemented method of claim 1, wherein the obtaining identified variant candidates comprises:
characterizing the identified non-primary peaks in both the forward orientation and the reverse orientation using at least one signal feature associated with the identified non-primary peaks in both the forward orientation and the reverse orientation, and
analyzing the at least one signal feature associated with identified non-primary peaks in both the forward orientation and the reverse orientation to identify the variant candidates.

7. The computer-implemented method of claim 1, further comprising:
minimizing noise in the test sample using a reference sample, the minimizing comprising:
removing, from the electropherogram sequence data of the test sample and electropherogram sequence data of the reference sample, primary sequence data to generate non-primary electropherograms for the test sample and the reference sample,
minimizing the difference between the non-primary electropherograms for the test sample and the reference sample by modifying the non-primary electropherogram for the reference sample, and
subtracting the modified non-primary electropherogram for the reference sample from an electropherogram for the test sample.

8. The computer-implemented method of claim 7, wherein the reference sample is a digital reference sample, wherein the digital reference sample is constructed from a first database of electropherograms with the same primary sequence as the test sample.

9. The computer-implemented method of claim 8, wherein the digital reference sample is digitally synthesized from a second database of electropherograms that do not have the same primary sequence as the test samples, wherein sequence fragments are woven together from the second database to construct a primary sequence that matches that of the test sample.

10. A non-transitory computer-readable storage medium encoded with instructions, executable by a processor, for determining minor variants of genetic material, the instructions comprising instructions for:
receiving electropherogram sequence data corresponding to a test sample from an electrophoresis sequencer that has performed electropherogram sequencing of the test sample in both a forward orientation and a reverse orientation, wherein the test sample includes the genetic material,
identifying any non-primary peaks in the electropherogram sequence data of the test sample in both the forward orientation and the reverse orientation,
obtaining identified variant candidates by, for each of a plurality of non-primary peaks in the forward orientation, confirming whether a non-primary peak is present at a complementary location in the reverse orientation, and determining a non-primary peak in the forward orientation to indicate a candidate variant if it is confirmed at the complementary location in the reversed orientation,
evaluating at least one peak characteristic of each of the identified variant candidates, and
classifying variant candidates as bona fide variants based on the evaluation of peak characteristics.

11. The non-transitory computer-readable storage medium of claim 10, further comprising instructions for:
receiving electropherogram sequence data corresponding to a reference sample.

12. The non-transitory computer-readable storage medium of claim 10, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature includes features used to compare the characteristics of one or more of the non-primary peaks to characteristics of one or more primary peaks.

13. The non-transitory computer-readable storage medium of claim 10, wherein the obtaining identified variant candidates comprises:
characterizing identified non-primary peaks in both the forward orientation and the reverse orientations using at least one signal feature associated with the identified non-primary peaks in both the forward orientation and the reverse orientations,
wherein the at least one signal feature includes features used to compare the characteristics of one or more of the non-primary peaks to characteristics of at least one primary peak under which at least one non-primary peak is positioned.

14. The non-transitory computer-readable storage medium of claim 10, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature is associated with the identified non-primary peaks of the test sample, further comprising instructions for:
identifying any non-primary peaks in electropherogram sequence data of a reference sample,
characterizing identified non-primary peaks of the reference sample using at least one signal feature associated with the identified non-primary peaks of the reference sample, and
analyzing the at least one signal feature associated with the identified non-primary peaks of the test sample and the at least one signal feature associated with the identified non-primary peaks of the reference sample to identify variant candidates in the test sample.

15. The non-transitory computer-readable storage medium of claim 10, wherein the obtaining identified variant candidates comprises:
characterizing the identified non-primary peaks in both the forward orientation and the reverse orientation using at least one signal feature associated with the identified non-primary peaks in both the forward orientation and the reverse orientation, and
analyzing the at least one signal feature associated with identified non-primary peaks in both the forward orientation and the reverse orientation to identify the variant candidates.

16. The non-transitory computer-readable storage medium of claim 10, further comprising instructions for:
minimizing noise in the test sample using a reference sample, the minimizing comprising:
removing, from the electropherogram sequence data of the test sample and electropherogram sequence data of the reference sample, primary sequence data to generate non-primary electropherograms for the test sample and the reference sample,
minimizing the difference between the non-primary electropherograms for the test sample and the reference sample by modifying the non-primary electropherogram for the reference sample, and
subtracting the modified non-primary electropherogram for the reference sample from an electropherogram for the test sample.

17. The non-transitory computer-readable storage medium of claim 16, wherein the reference sample is a digital reference sample, wherein the digital reference sample is constructed from a first database of electropherograms with the same primary sequence as the test sample.

18. The non-transitory computer-readable storage medium of claim 17, wherein the digital reference sample is digitally synthesized from a second database of electropherograms that do not have the same primary sequence as the test samples, wherein sequence fragments are woven together from the second database to construct a primary sequence that matches that of the test sample.

19. A system for determining minor variants of genetic material, the system comprising:
an electrophoresis sequencer configured to perform electropherogram sequencing of a test sample in both a forward orientation and a reverse orientation, wherein the test sample includes the genetic material;
a processor; and
a memory encoded with instructions, executable by the processor, the instructions for:
receiving electropherogram sequence data of the test sample in both the forward orientation and the reverse orientation,
identifying any non-primary peaks in the electropherogram sequence data of the test sample in both the forward orientation and the reverse orientation,
obtaining identified variant candidates by, for each of a plurality of non-primary peaks in the forward orientation, confirming whether a non-primary peak is present at a complementary location in the reverse orientation, and determining a non-primary peak in the forward orientation to indicate a candidate variant if it is confirmed at the complementary location in the reversed orientation,
evaluating at least one peak characteristic of each of the identified variant candidates, and
classifying variant candidates as bona fide variants based on the evaluation of peak characteristics.

20. The system of claim 19, wherein the memory encoded with instructions, executable by the processor, further comprises instructions for:
receiving electropherogram sequence data from a reference sample.

21. The system of claim 19, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature includes features used to compare the characteristics of one or more of the non-primary peaks to characteristics of one or more primary peaks.

22. The system of any claim 19, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature includes features used to compare the characteristics of one or more of the non-primary peaks to characteristics of at least one primary peak under which at least one non-primary peak is positioned.

23. The system of claim 19, wherein the obtaining identified variant candidates comprises:
characterizing identified non-primary peaks in both the forward orientation and the reverse orientations using at least one signal feature associated with the identified non-primary peaks in both the forward orientation and the reverse orientations, wherein the at least one signal feature is associated with the identified non-primary peaks of the test sample, and wherein the memory encoded with instructions, executable by the processor, further comprises instructions for:
identifying any non-primary peaks in electropherogram sequence data of a reference sample, characterizing identified non-primary peaks of the reference sample using at least one signal feature associated with the identified non-primary peaks of the reference sample, and analyzing the at least one signal feature associated with the identified non-primary peaks of the test sample and the at least one signal feature associated with the identified non-primary peaks of the reference sample to identify variant candidates in the test sample.

24. The system of claim 19, wherein the obtaining identified variant candidates comprises:

characterizing the identified non-primary peaks in both the forward orientation and the reverse orientation using at least one signal feature associated with the identified non-primary peaks in both the forward orientation and the reverse orientation, and analyzing the at least one signal feature associated with identified non-primary peaks in both the forward orientation and the reverse orientation to identify the variant candidates.

25. The system of claim 19, wherein the memory encoded with instructions, executable by the processor, further comprises instructions for:

minimizing noise in the test sample using a reference sample, the minimizing comprising:

removing, from the electropherogram sequence data of the test sample and electropherogram sequence data of the reference sample, primary sequence data to generate non-primary electropherograms for the test sample and the reference sample, minimizing the difference between the non-primary electropherograms for the test sample and the reference sample by modifying the non-primary electropherogram for the reference sample, and subtracting the modified non-primary electropherogram for the reference sample from an electropherogram for the test sample.

26. The system of claim 25, wherein the reference sample is a digital reference sample, wherein the digital reference sample is constructed from a first database of electropherograms with the same primary sequence as the test sample.

27. The system of claim 26, wherein the digital reference sample is digitally synthesized from a second database of electropherograms that do not have the same primary sequence as the test samples, wherein sequence fragments are woven together from the second database to construct a primary sequence that matches that of the test sample.

* * * * *